(12) United States Patent
Allen et al.

(10) Patent No.: US 11,508,168 B2
(45) Date of Patent: Nov. 22, 2022

(54) SYSTEMS AND METHODS FOR SPECIMEN INTERPRETATION

(71) Applicant: UPMC, Pittsburgh, PA (US)

(72) Inventors: Erastus Zachariah Allen, Pittsburgh, PA (US); Keith Michael Callenberg, Pittsburgh, PA (US); Liron Pantanowitz, Wexford, PA (US); Adit Bharat Sanghvi, Pittsburgh, PA (US)

(73) Assignee: UPMC, Pittsburgh, PA (US)

( * ) Notice: Subject to any disclaimer, the term of this patent is extended or adjusted under 35 U.S.C. 154(b) by 298 days.

(21) Appl. No.: 16/653,571

(22) Filed: Oct. 15, 2019

(65) Prior Publication Data

US 2020/0160032 A1 May 21, 2020

Related U.S. Application Data

(60) Provisional application No. 62/745,961, filed on Oct. 15, 2018.

(51) Int. Cl.

| | |
|---|---|
| *G06K 9/00* | (2022.01) |
| *G06V 20/69* | (2022.01) |
| *G06N 3/04* | (2006.01) |
| *G16H 30/20* | (2018.01) |

(Continued)

(52) U.S. Cl.
CPC ......... *G06V 20/698* (2022.01); *G06N 3/0454* (2013.01); *G06T 7/0012* (2013.01); *G06T 7/70* (2017.01); *G06V 20/695* (2022.01); *G16H 30/20* (2018.01); *G06T 2207/30024* (2013.01)

(58) Field of Classification Search
CPC ............ G06K 9/00147; G06K 9/0014; G06K 9/4652; G06N 3/0454; G06N 3/08; G06N 7/005; G06N 20/20; G06T 7/0012; G06T 7/70; G06T 2207/30024; G06T 2207/10056; G06T 2207/20076; G06T 2207/20081; G06T 2207/20084; G16H 30/20; G16H 30/40; G16H 50/30; G16H 50/20; Y02A 90/10

See application file for complete search history.

(56) References Cited

U.S. PATENT DOCUMENTS

| | | | | |
|---|---|---|---|---|
| 6,519,355 | B2 * | 2/2003 | Nelson ................. | G01N 15/147 |
| | | | | 382/133 |
| 6,636,623 | B2 * | 10/2003 | Nelson ............... | G01N 15/1475 |
| | | | | 382/133 |

(Continued)

OTHER PUBLICATIONS

Callenberg et al., "Analysis of Cell Galleries as an Interface for Reviewing Urine Cytology Cases," Presented at Proceedings of the Pathology Informatics Summit 2019, Pittsburgh, PA, May 5-9, 2019, 14 pages.

(Continued)

*Primary Examiner* — Tom Y Lu

(74) *Attorney, Agent, or Firm* — Fish & Richardson P.C.

(57) ABSTRACT

Systems, methods, devices, and other techniques using machine learning for interpreting, or assisting in the interpretation of, biologic specimens based on digital images are provided. Methods for improving image-based cellular identification, diagnostic methods, methods for evaluating effectiveness of a disease intervention, and visual outputs useful in assisting professionals in the interpretation of biologic specimens are also provided.

23 Claims, 16 Drawing Sheets

(51) Int. Cl.
*G06T 7/00* (2017.01)
*G06T 7/70* (2017.01)

(56) References Cited

U.S. PATENT DOCUMENTS

| | | | | |
|---|---|---|---|---|
| 6,897,875 | B2* | 5/2005 | Zhang | G06K 9/6253 345/587 |
| 7,587,078 | B2* | 9/2009 | Zahniser | G01N 15/1475 382/133 |
| 7,856,136 | B2* | 12/2010 | Lee | G06T 7/0012 382/133 |
| 8,116,551 | B2* | 2/2012 | Gallagher | G06K 9/0014 382/133 |
| 9,842,391 | B2 | 12/2017 | Tunstall et al. | |
| 9,984,199 | B2 | 5/2018 | Sood et al. | |
| 2018/0122508 | A1 | 5/2018 | Wilde et al. | |
| 2018/0204048 | A1 | 7/2018 | Chefd'hotel et al. | |

OTHER PUBLICATIONS

Callenberg et al., "Investing in Computation for the Future of Health Care." Presented at Proceedings of the Computational Medicine Conference, Pittsburgh, PA, Oct. 29, 2019, 41 pages.
Callenberg, "Artificial Intelligence Tools Under Development at UPMC," Presented at Proceedings of the Association for Pathology Informatics Digital Pathology and AI Workshop III, Pittsburgh, PA, Dec. 13-14, 2019, 37 pages.
Pantanowitz, "AI and Cytopathology," Presented at the Memorial Sloan Kettering Cancer Center, New York City, NY, Nov. 2019, 17 pages.
Sanghvi et al., "Analysis of Cell Galleries as an Interface for Reviewing Urine Cytology Cases," J. Pathol. Informatics, Sep. 16, 2019, 10(28):S32.
Sanghvi, "UPMC Enterprises Overview," Presented at Carnegie Mellon University, Pittsburgh PA, Apr. 18, 2018, 20 pages.
Bankhead et al., "QuPath: Open source software for digital pathology image analysis." Scientific Reports, 2017, 7(1):16878, 7 pages.
Barkan et al., "The Paris System for Reporting Urinary Cytology: The Quest to Develop a Standardized Terminology," Acta Cytol, 2016, 60(3):185-97.
Brimo et al., "Suspicious for High-Grade Urothelial Carcinoma (Suspicious)," The Paris System for Reporting Urinary Cytology, 2016, 49-60.
Bulletin.cytopathology.org [online], "Innovation," Nov. 1, 2019, retrieved on Jan. 29, 2021, retrieved from URL<https://bulletin.cytopathology.org/innovation-2/>, 5 pages.
DeLong et al., "Comparing the Areas Under Two or More Correlated Receiver Operating Characteristic Curves: A Nonparametric Approach," Biometrics, 1988, 44(3):837-45.
Dey et al., "Artificial Neural Network in Diagnosis of Lobular Carcinoma of Breast in Fine-Needle Aspiration Cytology," Diagnostic Cytopathology, 2013, 41(2):102-6.
Dimashkieh et al., "Evaluation of UroVysion and Cytology for Bladder Cancer Detection," Cancer Cytopathology, 2013, 121(10):591-597.
Donnelly et al., "Optimal z-axis scanning parameters for gynecologic cytology specimen," J Pathol Inform, Dec. 2013, 4(1):38, 17 pages.
Gelwan et al., "Variability among observers utilizing the CellSolutions BestCyte Cell Sorter imaging system for the assessment of urinary tract cytology specimens." J Am Soc Cytopathol, 2019, 8(1):18-26.
Hang et al., "Digital Image Analysis Supports a Nuclear-To-Cytoplasmic Ratio Cutoff Value of 0.5 for Atypical Urothelial Cells," Cancer Cytopathology, 2017, 125(9):710-6.
Janowczyk et al., "Deep learning for digital pathology image analysis: A comprehensive tutorial with selected use cases," J Pathol Inform, Jul. 2016, 7:29, 39 pages.

Layfield et al., "Accuracy and Reproducibility of Nuclear/Cytoplasmic Ratio Assessments in Urinary Cytology Specimens," Diagnostic Cytopathology, 2017, 45(2):107-12.
Lee et al., "Causes of false-negative for high-grade urothelial carcinoma in urine cytology," Diagnostic Cytopathology, 2016, 44(12):994-9.
Long et al., "Interobserver reproducibility of The Paris System for Reporting Urinary Cytology," CytoJournal, 2017, 14:17, 17 pages.
Martinez et al., "VIPS—a highly tuned image processing soil ware architecture," IEEE International Conference on Image Processing, 2005, 4 pages.
McCroskey et al., "Accuracy and Interobserver Variability of the Cytologic Diagnosis of Low-Grade Urothelial Carcinoma in Instrumented Urinary Tract Cytology Specimens," Am J Clin Pathol, 2015, 144(6):902-8.
McIntire et al., "Digital Image Analysis Supports a Nuclear-to-Cytoplasmic Ratio Cutoff Value Below 0.7 for Positive for High-Grade Urothelial Carcinoma and Suspicious for High-Grade Urothelial Carcinoma in Urine Cytology Specimens," Cancer Cytopathology, 2019, 127(2):120-4.
McIntire et al., "Negative Predictive Value and Sensitivity of Urine Cytology Prior to Implementation of The Paris System for Reporting Urinary Cytology," Cancer Cytopathol, 2019, 127(2):125-31.
Melder et al., "Automated image analysis in the diagnosis of bladder cancer," Appl Opt, 1987, 26(16):3367-72.
Mitchell et al., "Improving the digital cytology review experience may lead to increased efficiency." J Am Soc Cytopathol, 2018, 7(5):S65.
Momeni-Boroujeni et al., "Computer-Assisted Cytologic Diagnosis in Pancreatic FNA: An Application of Neural Networks to Image Analysis," Cancer Cytopathology, 2017, 125(12):926-33.
Mukherjee et al., "Investigation of scanning parameters for thyroid fine needle aspiration cytology specimens: A pilot study," J Pathol Inform, 2015, 6(1):43, 15 pages.
Northrup et al., "Clinical follow up and the impact of the Paris system in the assessment of patients with atypical urine cytology," Diagnostic Cytopathology, 2018, 46(12):1022-30.
Pantanowitz et al., "Community Crowdsourcing Tool to Expedite Annotations for Deep Learning in Pathology," J Pathol Inform, 2018, 9(50):S14.
Pantanowitz, "Automated pap tests," Practical Informatics for Cytopathology, Jan. 2014, 14:147-155.
Pantazopoulos et al., "Back propagation neural network in the discrimination of benign from malignant lower urinary tract lesions," J Urol, 1998, 159(5):1619-23.
PCT International Search Report and Written Opinion in International Appln. No. PCT/US2019/056222, dated Feb. 11, 2020, 10 pages.
Quick Compendium of Cytopathology, 1st ed., Khalbuss et al. (eds.), Jun. 2013, 183-210.
Reid et al., "Accuracy of grading of urothelial carcinoma on urine cytology: an analysis of interobserver and intraobserver agreement," Int J Clin Exp Pathol, 2012, 5(9):882-91.
Sanghvi et al., "AI Meets Cytology," Presented to the University of Pittsburgh Intelligent Systems Program, Nov. 2, 2018, 34 pages.
Sanghvi et al., "Performance of an Artificial Intelligence Algorithm for Reporting Urine Cytopathology," Cancer Cytopathology, Oct. 2019, 127(10:658-666.
Song et al., "Accurate Segmentation of Cervical Cytoplasm and Nuclei Based on Multiscale Convolutional Network and Graph Partitioning," IEEE Trans Biomed Eng, 2015, 62(10):2421-33.
Sundling et al., "PST154: Refinement of Convolutional Neural Networks for Urine Cytology Prescreening." J. Am. Soc. Cytopathology, Sep. 2017, 6(5):S65.
Vaickus et al., "Automating the Paris System for Urine Cytopathology—A Hybrid Deep-Learning and Morphometric Approach," Cancer Cytopathology, 2019, 127(2):98-115.
Van Der Poel et al., "Conventional Bladder Wash Cytology Performed by Four Experts versus Quantitative Image Analysis," Mod Pathol, 1997, 10(10):976-82.
VandenBussche, "A review of the Paris system for reporting urinary cytology," Cytopathology, 2016, 27(3):153-6.

(56) References Cited

OTHER PUBLICATIONS

Vrieseima et al., "Neural Network-Based Digitized Cell Image Diagnosis of Bladder Wash Cytology," Diagnostic Cytopathology, 2000, 23(3):171-9.

Wied et al., "Artificial intelligence-guided analysis of cytologic data," Anal. Quant. Cytol. Histology, 1990, 12(6):417-428.

William et al., "A review of image analysis and machine learning techniques for automated cervical cancer screening from pap-smear images," Comput. Methods Programs Biomedicine, 2018, 164:15-22.

* cited by examiner

SYSTEMS AND METHODS FOR SPECIMEN INTERPRETATION

RELATED APPLICATIONS

This application claims priority under 35 USC § 119(e) to provisional U.S. Patent Application 62/745,961, filed on Oct. 15, 2018, the entire contents of which is hereby incorporated by reference.

TECHNICAL FIELD

This document relates to the interpretation of biologic specimens using digital images.

BACKGROUND

Cytology interpretations are traditionally performed by cytotechnicians and cytopathologists. Typically, cells in specimens are manually reviewed under a microscope and evaluated according to established criteria for a suspected disease or condition. Similarly, histologists traditionally manually review tissue specimens using microscopy. Manual review can require extended amounts of time. In some cases, due to time constraints, manual reviewers may limit the number of cells or tissue portions reviewed in a given specimen, thereby decreasing accuracy. Additionally, specimen characterization of a single specimen often differs across different manual reviewers.

SUMMARY

This document discloses systems, methods, devices, and other techniques for interpreting, or assisting in the interpretation of, biologic specimens based on digital images. Methods for improving for improving image-based cellular identification, diagnostic methods, methods for evaluating effectiveness of a disease intervention, and visual outputs useful in assisting professionals in the interpretation of biologic specimens are also provided.

In one aspect, a method is provided, comprising identifying, by a system of one or more computers, a feature vector that represents cytomorphologic criteria for each of one or more individual cells within a plurality of cells in at least a portion of a whole specimen slide image; generating, by the system, for each of the one or more individual cells, an array of feature scores, wherein the array of feature scores comprises a score for each of a plurality of features in the feature vector; determining, by the system, a presence or absence of a disease or disease type for the whole specimen slide based on the array of feature scores; and providing, by the system, an output indicative of the presence or absence of a disease or disease type for the whole specimen slide.

In some embodiments, the method can further include, prior to identifying the feature vector, receiving, by the system, an image of a whole specimen slide comprising a plurality of biological cells; detecting, by the system, at least a portion of each of one or more individual cells within the plurality of cells; and determining, by the system, spatial coordinates for each of the one or more individual cells. In some embodiments, the method can further include extracting, by the system, for each of the one or more individual cells, an extracted image of the individual cell, wherein the cell is centered on the extracted image, each extracted image representing an independent individual cell. In some embodiments, the method can further comprise processing, by the system, the one or more extracted images to generate a cell type score for each extracted image; and extracting, by the system, a set of one or more of the extracted images having a cell type score within a predetermined range, wherein the cell type score represents an estimate of the likelihood that the cell is a target cell type.

In some embodiments, the methods can further include one or more of the following features. The method can further comprise ranking, by the system, each cell represented in the array of feature scores based on the array of feature scores. The method can further comprise classifying, by the system, using a gaussian mixture model, each cell represented in the array of feature scores into one of a plurality of predetermined cell-type clusters based on the array of feature scores. Each feature score can be determined by an independent machine learning model. The plurality of features can include one or more cell-level features selected from a plurality of cytomorphologic criteria. Processing the array of feature scores can further comprise determining, by the system, a first set of metrics from the array of feature scores; generating, by the system, based on the first set of metrics, an aggregated vector of integer or floating point numbers representing the whole specimen slide; and processing, by the system, the aggregated vector in a machine learning model. The first set of metrics can include summary statistics selected from the group consisting of mean, median, standard deviation, variance, kurtosis, or skew, histograms, principal components analysis, and combinations thereof. The one or more outputs can be selected from the group consisting of summary statistics, a cell type cluster score, one or more feature scores, an image of each of one or more cells, a composite image having a plurality of images of multiple cells, and combinations thereof. The method can further comprise, prior to processing the one or more extracted images, removing, by the system, background noise in each extracted image in the set. Generating the array of feature scores can include extracting each of a plurality of features; and independently processing, by the system, each extracted feature in an independent machine learning model to generate a score for each of the features.

In another aspect, a method is provided, including identifying, by a system of one or more computers, a feature vector that represents cytomorphologic criteria for each of one or more individual cells within a plurality of cells in a whole specimen slide image; generating, by the system, for each of the one or more individual cells, an array of feature scores, wherein the array of feature scores comprises a score for each of a plurality of features in the feature vector; processing, by the system, the array of feature scores to identify one or more diagnostic cells within the plurality of cells, wherein the one or more diagnostic cells are useful for determining the presence or absence of a disease or disease type; and providing, by the system, one or more outputs indicative of the one or more diagnostic cells.

In another aspect, a method is provided, including receiving, by a system of one or more computers, an image of a whole specimen slide comprising a plurality of biological cells; detecting, by the system, at least a portion of each of one or more individual cells within the plurality of cells; determining, by the system, spatial coordinates for each of the one or more individual cells; extracting, by the system, for each of the one or more individual cells, an extracted image of the individual cell, wherein the cell is centered on the extracted image, each extracted image representing an independent individual cell; processing, by the system, the one or more extracted images to generate a cell type score for each extracted image; extracting, by the system, a set of one or more of the extracted images having a cell type score within a predetermined range; processing, by the system, each of the one or more extracted images within the set to generate an array of feature scores, wherein the array of feature scores comprises, for each image, a score for each of a plurality of features in a feature vector generated from the extracted image; determining, by the system, a first set of metrics from the array of feature scores to generate an aggregated vector of integer or floating point numbers representing the whole specimen slide; and processing, by the system, the aggregated vector in a classifier to generate an output indicative of the presence or absence of a disease or disease type for the whole specimen slide.

In another aspect, a method of diagnosing, in a subject, a condition selected from the group consisting of high grade urothelial carcinoma, suspicious for high grade urothelial carcinoma, low grade urothelial neoplasia, atypical urothelial cells, and negative for high grade urothelial carcinoma is provided, including determining the presence or absence of a disease or disease type according to any one of the methods described herein.

In another aspect, a method of evaluating the effectiveness of a cancer intervention measure in a subject having or at risk for developing a cancer is provided, including determining the existence of cancerous or precancerous cells according to the methods described herein; applying at least one intervention measure that is commensurate with the treatment or prevention of the cancer; and determining the effectiveness of the intervention measure.

In another aspect, a visual interface is provided, including an image of a whole specimen slide including biological cells, overlaid with a visual representation of a prediction score for each of one or more cells identified in the slide. In some embodiments, the prediction score can provide a visual indication of an importance score for each identified cell based on the cell's importance in determining the presence or absence of a disease or disease type. In some embodiments, the prediction score can provide a visual indication of a point on a severity scale indicative of a severity of a disease or disease type.

In another aspect, a visual interface is provided, including a single composite image comprising a plurality of selected individual cell images extracted from at least a portion of a whole specimen slide image comprising a plurality of cells.

The systems, methods, and other techniques described herein provide several advantages. First, automated analyses of biologic specimens, whether for diagnostic or assistive purposes, can decrease the time and costs of the methods and systems described herein as compared to traditional methods. In some implementations, the systems, methods, and other techniques described herein can provide professionals with limited, targeted, cells or tissue portions for human review, thus decreasing the review time by focusing the professional toward only the portions important for clinical interpretation. In other implementations, the systems, methods, and other techniques described herein can provide full diagnostics or diagnostic support, virtually eliminating human review. Thus the systems, methods, and other techniques described herein can also limit the need for cost- and time-intensive training of clinicians and other professionals that traditionally interpret the specimens.

Second, some implementations of the systems, methods, and other techniques described herein can improve accuracy of interpretation. Automated review can allow for evaluation of more cells or specimens than is traditionally possible for cytopathologists. Additionally, some implementations of the systems, methods, and other techniques described herein can provide evaluation of parameters or criteria not traditionally or not feasibly reviewed in traditional interpretation methods.

Third, the systems, methods, and other techniques described herein can provide improved consistency of specimen interpretations, and improved consistency specimen quality measurements, such as sample degradation, cell count adequacy, and image focus quality.

Fourth, some implementations of the systems, methods, and other techniques described herein can be adapted across multiple specimen types and disease types.

Fifth, the systems, methods, and other techniques described herein advantageously pair existing clinical knowledge and guidelines for specimen evaluation and diagnosis with automated machine learning systems to increase the accuracy of automated evaluation. Additionally, the exiting clinical knowledge and guidelines can be paired with new evaluative parameters that are only practically available for evaluation in automated systems, thus improving the overall accuracy as compared to traditional clinical evaluation. Further, the systems, methods, and other techniques described herein allow for hybrid evaluation, in which the automated system assists a clinical professional in joint interpretation of a specimen. For example, in some implementations, an automated system can provide a clinician or other professional with a subset of specimen portions or images that the automated system has identified as important in evaluating the specimen. The clinician or other professional can then focus the evaluation on the identified portions, thus incorporating both machine and human intelligence to provide greater accuracy over methods performed by humans or automate systems alone.

Sixth, the systems, methods, and other techniques described herein surprisingly can distinguish, classify, and score overlapping cells. In some portions of a slide, two or more cells may overlap, sometimes causing their exclusion from analysis or an incorrect analysis. Developing an explicit algorithm for overlapping cells has continued to prove difficult. The multi-tiered approach of systems, methods, and other techniques described herein, in which cytomorphologic criteria are analyzed, allows training of the systems such that overlapping cells can be included in the analysis of disease and disease type. For example, in some embodiments, supervised training on images having overlapping cells allows the systems to provide meaningful data or characteristics of a selected cell despite overlap between two or more cells.

Seventh, the systems, methods, and other techniques described herein advantageously process the cells and provide the desired output despite image aberrations in the image.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

For the terms "for example" and "such as," and grammatical equivalences thereof, the phrase "and without limitation" is understood to follow unless explicitly stated otherwise. As used herein, the term "about" is meant to account for variations due to experimental error. As used herein, the singular forms "a," "an," and "the" are used interchangeably and include plural referents unless the context clearly dictates otherwise.

Also herein, the recitations of numerical ranges by endpoints include all numbers subsumed within that range (e.g., 1 to 5 includes 1, 1.5, 2, 2.75, 3, 3.80. 4, 5, etc.). Other features and advantages of the invention will be apparent from the following detailed description and figures, and from the claims.

DETAILED DESCRIPTION

Figure 1:
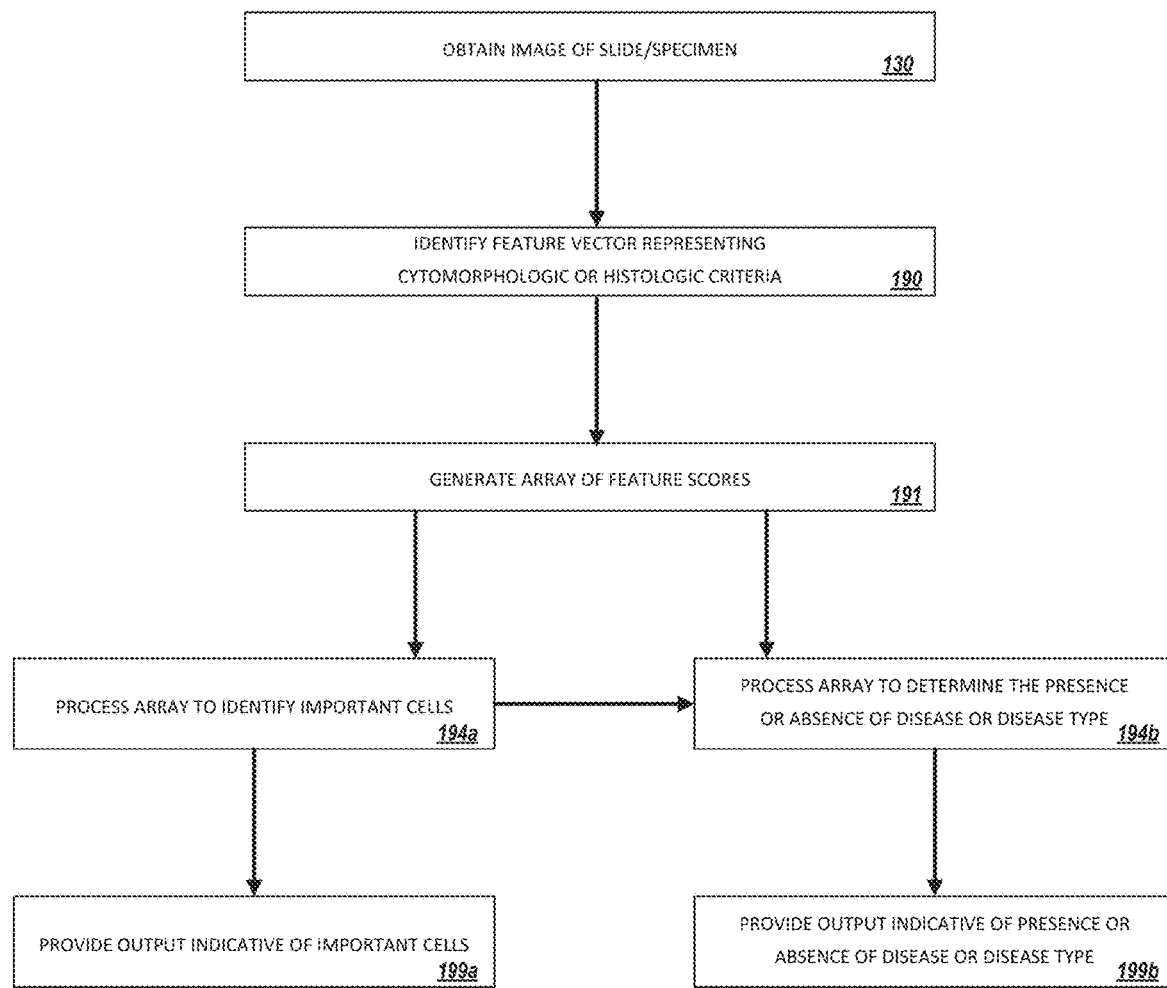
FIG. 1 is a flow chart of an exemplary method for interpreting a digital image of a slide or specimen.

This document provides systems, methods, devices, and other techniques for interpreting, or assisting in the interpretation of, biologic specimens based on digital images. In some implementations, digital specimen images can be processed in a cell diagnosis or tissue diagnosis machine learning system. In some implementations, a system is composed of an ensemble of machine learning algorithms that have been trained using pathologist annotations. In some implementations, the system can further include a cell identifier. In some implementations, methods for improving image-based cellular identification are provided. In some implementations, diagnostic methods and methods for evaluating effectiveness of a disease intervention are provided. In some implementations, visual outputs useful in assisting professionals in the interpretation of biologic specimens can be created.

As described herein machine learning systems are used to interpret, or assist in the interpretation of biological specimens. The systems, methods, devices, and other techniques described herein advantageously differ from ordinary machine learning classification systems. In traditional systems, specimens are simply presented to a machine learning system and trained based on the final output. For example, a traditional system may present a digital specimen image to a machine learning system for training; training may simply involve a professional, such as a pathologist, providing a final diagnostic. Thus, traditional diagnostic machine learning systems and methods omit existing clinical knowledge and training/learning opportunities.

In the systems and methods described herein, a multi-tiered process is used to instead incorporate the existing body of knowledge of clinical features, guidelines, and practice standards such that the body of clinical knowledge is built into the systems and methods. The system can therefore be trained on the individual features—the reasons for the final clinical diagnosis—as well as the final diagnosis, and those features are then compiled to be processed into the final diagnosis. Thus, in some embodiments, the systems and methods described herein do not utilize conventional end-to-end deep learning, but instead use a multi-tiered approach of multiple levels of machine learning.

Additionally, this multi-tiered approach allows flexibility in developing, training, and adapting systems such as those described herein by providing opportunities to gather additional data at different tiers of the analysis, including data that is useful in understanding the systems and training for final diagnosis, but also data useful in its own right, such as for improving and optimizing system outputs. For example, data may be gathered that can be useful in optimizing the type or amount of data presented to a clinician when the clinician is using the system and its output to aid in clinical diagnosis or prognosis. As another example, the systems can provide such data as counts of cells having a certain feature score. Such data was previously unobtainable in a practical sense without systems such as those described herein, and can have utility for the development of systems such as those described herein, or for the diagnostic determinations made by the systems and methods described herein. Additionally, such data can have utility outside of the systems and methods described herein, such as for research purposes.

In some embodiments, the methods or processes described herein generally involve whole slide classification using clinically-relevant cellular features, such as cytomorphologic or histologic criteria. The methods use deep learning to predict whole slide-level pathology diagnoses based on aggregated cellular features chosen from, e.g., established guidelines or clinical practice. Deep learning is often considered an uninterpretable black box process. There are a number of approaches for explaining the behavior of deep learning-based machine learning models, but these are nearly all retrospective and limited. In order to take advantage of deep learning while maintaining interpretability, the approach described herein includes a separate deep learning-based sub-model trained for each cellular feature deemed relevant for a particular interpretation by clinical guidelines, providing a first tier of analysis. The results of these sub-models are then aggregated for all cells or tissue across the whole slide image using statistical summary measures (e.g. mean, standard deviation, skew). These statistical measures, as well as, in some embodiments, other additional data, can then be used in a second tier of machine learning analysis to predict a whole slide-level diagnosis, such as the presence or absence of a disease or disease type. This method is not only accurate, but also enables display of the reasoning for the diagnosis at the cellular and whole slide levels, and allows for optimization of outputs as well as optimization of the system models.

FIG. 1 is a flow chart of an exemplary method 100 for interpreting a digital image of a slide or specimen. The process of FIG. 1 can be performed by one or more computers in one or more locations, such as in the system depicted in FIG. 2. The process represented in FIG. 1 will be explained by way of example with reference to FIG. 2.

At stage 130, the system obtains an input image of a slide or slide portion prepared from a biological sample or specimen. The image can be obtained from an existing image, such as image 220b in FIG. 2. Existing images can be previously obtained images taken of specimen samples obtained from one or more subjects in the near or distant past. In some embodiments, an existing image can be obtained from a remote location or clinic for processing at a facility having the system. The image can also be obtained, for example, as image 220a in FIG. 2, from a slide 206 prepared from a recent specimen 205 obtained from a subject 202. The image can be obtained by any slide imaging process. For example, a digital slide imager 210, as in FIG. 2, may be used to create image 220a. However, other imagers and methods may be used, such as a digital camera mounted to a microscope.

Any type of cell-containing or tissue-containing specimen can be used to produce or obtain the image. For example, useful specimens can include a urine sample, a blood sample, a saliva sample, a biopsy, fine needle aspirates (e.g., from thyroid cysts, pancreatic cysts, and the like), body fluid samples (e.g., samples from pleural effusions), scrapings (e.g., a Tzank smear), resections, frozen sections, inflammatory exudate samples (e.g., pus), semen samples, samples of bodily secretions (e.g., sweat), bile duct brushing samples, autopsy samples, and the like. The specimen mounted on the slide can be in original, processed, or purified form, and can include suitable buffers or other reagents useful in the imaging and analysis process. Buffer and reagents can include those known in the art for analysis of various desired diseases, conditions, conditions, or cellular processes.

In some embodiments, an obtained image can be a training image specifically chosen for purposes of training the system. For example, the image can be of a slide prepared from a specimen or mixture of specimens that has been enriched, purified, or otherwise particularly chosen to represent a specific disease, disease type, condition, cell, cell type, or the like.

Figure 2:
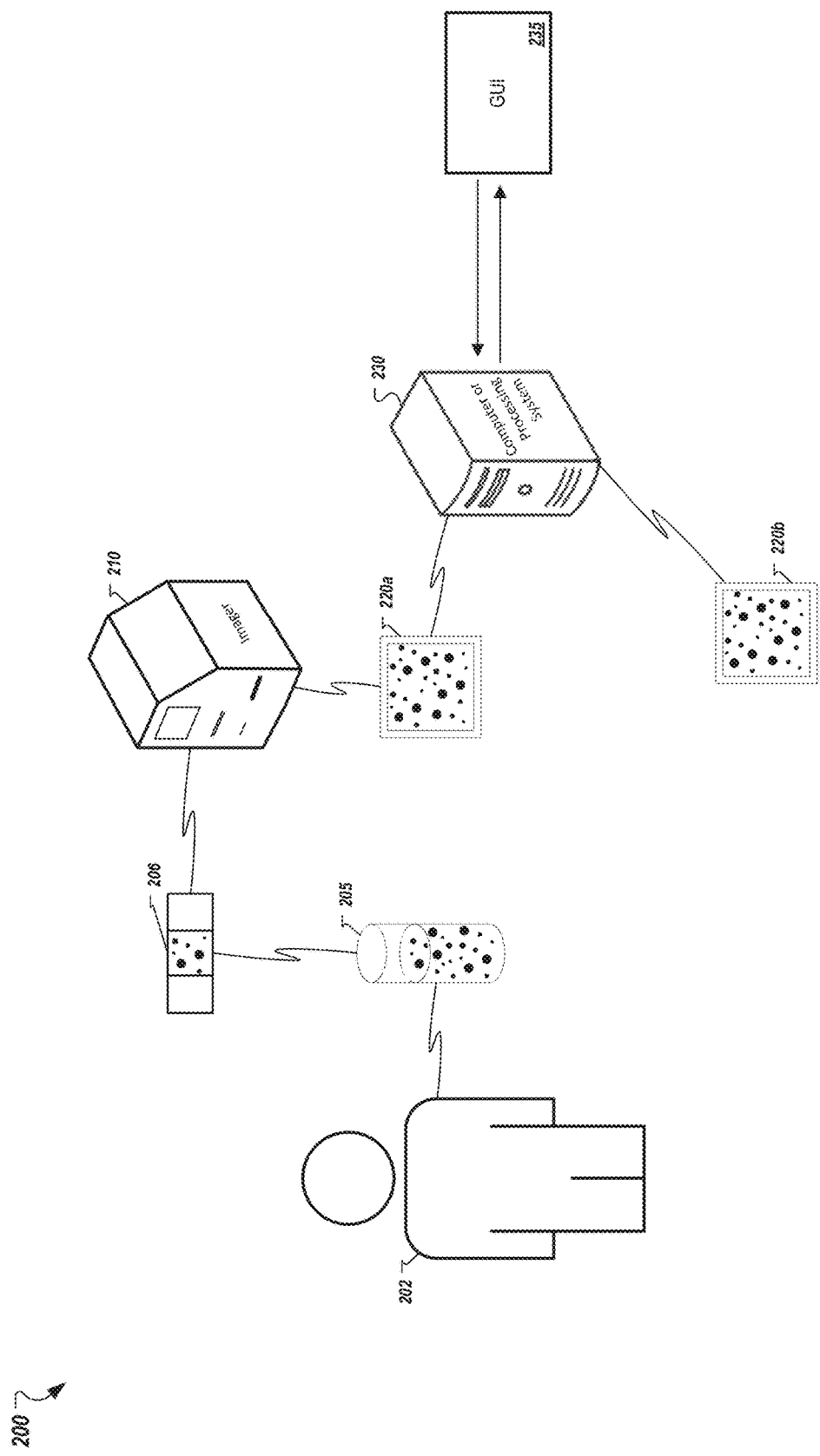
FIG. 2 is a block diagram depicting an exemplary system and method for interpreting a digital image of a slide or specimen.

At stage 190, once the computer or processing system, e.g., system 230 in FIG. 2, receives or obtains the image, a feature vector can be identified. The feature vector can be representative of cytomorphologic or histologic criteria. For example, two or more features based on two or more cytomorphologic or histologic criteria can be used to identify the feature vector. In some embodiments, the features can be based on clinical guideline features typically used by human pathologists and other professionals to interpret specimens. In some embodiments the features are or are representative of cytomorphologic or histologic criteria used in diagnostic pathology methods. For example, a feature vector can be based on criteria from standardized clinical guidelines that are or are representative of cytomorphologic criteria for reporting urinary cytology, such as the PARIS system for reporting urinary cytology (PARIS). As another non-limiting example, a feature vector can be based on criteria from standardized clinical guidelines that are or are representative of cytomorphologic criteria for cervical, anal, or vaginal cytology, such as the Bethesda system for reporting cervical and vaginal cytology. In some embodiments the features are or are representative of cytomorphologic criteria set forth in standardized pathology systems, such as in the Bethesda system for thyroid cytology, the Milan system for salivary gland cytology, the Papanicolaou Society of Cytopathology guideline for pancreatobiliary cytology, the Papanicolaou Society of Cytopathology guideline for respiratory cytology, International Academy of Cytology standardized reporting of breast fine-needle aspiration biopsy cytology. In some embodiments, the features are or are representative of cytomorphologic criteria in reporting systems for lymph nodes or body fluids/effusions. In some embodiments, one or more features of the feature vector can be a non-standardized clinical guideline, feature, or criteria of cytologic or histologic relevance.

In some embodiments, the features can be selected from cell-level features, slide-level features, or combinations thereof. Cell-level features include features that can be identified or examined for a given single cell, such as cytomorphologic criteria. For example, in some embodiments, cell level features can include a nuclear-to-cytoplasmic ratio, nuclear hyperchromasia, chromatin coarseness, nuclear membrane irregularity, cellular degradation, malignancy classifier, malignancy value, focal score, nuclear-to-cytoplasmic pixel ratio, cell-in-cell arrangements, and the like, and combinations thereof.

In some embodiments, the features can be selected from slide-level features. Slide-level features include features that can be identified or examined for a whole slide image or portion of a slide image. For example, in some embodiments slide-level features can include cell count, cell type count (e.g., target cell type count), target cell type proportion, total cells in slide, atypical cell count, atypical cell proportion, malignant cell count, cell-in-cell arrangement count, degraded cell proportion, a cell cluster analysis parameter, and the like, and combinations thereof. In some embodiments, slide-level features can include urothelial cell count, urothelial cell proportion, total cells in slide, atypical cell count, atypical cell proportion, malignant cell count, and degraded cell proportion.

At stage 191, the system can generate an array of feature scores. The scores can be based on training received by the system. For example, a system can be trained against a pathologist's scores for each selected features, based on the particular representative feature and disease, condition, or process being examined. For example, a series of trained models can be used to produce an array of feature scores including scores for each of the selected features. One skilled in the art will appreciate that any of the various methods available for training one or more models for the systems and methods described herein may be used. In some embodiments, the systems, methods, and devices described herein can use deep learning. In some embodiments, the systems, methods, and devices described herein do not use simple end-to-end learning to analyze a slide image. In some embodiments, the systems, methods, and devices described herein use a first tier of trained models (e.g., a series of models including one or more models for each of two or more features), combined with a second tier trained model that processes an array of feature scores obtained from the first tier of models. In some embodiments, the systems, methods, and devices described herein use machine learning to perform one or more of classification, regression, clustering, and association. In some embodiments, the systems, methods, and devices described herein can employ one or more of dynamic time warping (DTW), decision trees, linear regression, neural networks, multinomial LR, Naive Bayes (NB), trained Gaussian NB, NB with dynamic time warping, MLR, Shannon entropy, support vector machine (SVM), one versus one support vector machine, k-means clustering, Q-learning, temporal difference (TD), deep adversarial networks, and the like. In some embodiments, the systems and methods described herein use one or more multiple instance learning models.

In some embodiments, the array of feature scores can be processed, as at stage 194*a*, to identify cells considered to be important in the clinical diagnosis of or prognosis for a disease, disease type, condition, or biological process. In some embodiments, cells considered to be important can be determined by comparing individual or combined feature scores against a predetermined threshold. In some embodiments, cells considered to be important can be determined based on learned analysis the computer system. In some embodiments, important cells can include cells meeting non-specific parameters such as quality of the cell or cell image based on, e.g., degradation, focus quality, and the like. In some embodiments, important cells can include cells meeting specific parameters such as disease-specific feature score thresholds.

In one example, of the method, the system can process one or more images or extracted images to generate a cell type score for each extracted image (toward the goal of identifying the cell type, such as urothelial cells). Next, the method can include extracting, by the system, a set of one or more of the extracted images having a cell type score within a predetermined range. In some embodiments, these extracted images can be considered by the system as including important cells for evaluation or output. In this example, the cell type score can represent an estimate of the likelihood that the cell is a target cell type. The target cell type can be any cell type. In some cases, the target cell type may be relevant for diagnosis and selected for further review. In other cases, the target cell type can be considered irrelevant and selected for removal from the analysis. In some embodiments, the target cell type is selected from the group consisting of urothelial cells, squamous epithelial cells, basal cells, follicular cells, glomerular cells, glandular cells, lymphocytes, monocytes, neutrophils, eosinophils, and combinations thereof. In some exemplary embodiments, the method can further comprise ranking, by the system, each cell represented in the array of feature scores based on the array of feature scores. The ranking of each cell represented in the array of feature scores based on the array of feature scores comprises ranking based on one or more feature scores within the array of feature scores. The method can further comprising selecting, by the system, a subset of cells represented in the array of feature scores based on a predetermined ranking range. In some embodiments, ranking can use other, orthogonal data besides or in conjunction with the array of features scores. In some embodiments, the ranking can be based on a single feature score or a combination of feature scores. In some embodiments, the ranking can be used to filter out degraded cells from the analysis. In some embodiments, this subset can represent important cells for further analysis or output.

In some embodiments, the system can provide an output (via, e.g., a graphical user interface (GUI) 235 as in FIG. 2), as at stage 199*a*, indicative of the cells identified as important. In some embodiments, the output can provide textual, graphical, numeric, or photographic representation of the cells and/or the cells' feature scores. In some embodiments, the output can include an image of the whole slide overlaid with a form of highlighting (e.g., outline, color or shade differentiation, etc.) identifying the important cells. In some embodiments, the output can include one or more images of one or more important cells. In some embodiments, the output can include a gallery of images of important cells. In some embodiments, the output can include a virtual slide image compiling the images of the important cells. Virtual slide image can include a single image that is a single compiled image created from images of multiple cells (for example, images of multiple cells within the original slide image). In some embodiments, the output indicative of the important cells can be used by a pathologist or other clinician or professional to verify a machine-provided or system-provided clinical diagnosis or indication of the presence or absence of a disease or disease type. In some embodiments, the output indicative of the important cells can be used by a pathologist or other clinician or professional to determine a clinical diagnosis or indication of the presence or absence of a disease or disease type. In some embodiments, the output indicative of the important cells can be used by a pathologist or other clinician or professional to prescribe a treatment or other tests deemed necessary or useful in determining a clinical diagnosis or indication of the presence or absence of a disease or disease type.

In some embodiments, the array of feature scores can be processed to determine a clinical diagnosis or the presence or absence of a disease or disease type. In some embodiments, the presence or absence of a disease can include a clinical diagnosis that a subject or specimen or image is positive or negative or inconclusive for a specific disease or condition, such as the diseases disclosed herein. In some embodiments, the presence or absence of a disease can include a suspected clinical diagnosis that can be used in conjunction with other clinical analyses to make a final diagnosis that a subject or specimen or image is positive or negative or inconclusive for a specific disease or condition. In some embodiments, the presence or absence of a disease type can include a distinction of a severity of a disease (e.g., stage 1, 2, 3, or 4 cancer; pre-cancer; hyperplasia; etc.). In some embodiments, the presence or absence of a disease or disease type can include an estimate of the presence, absence, or likelihood of development of a disease or disease type. In some embodiments, the presence or absence of a disease or disease type is not a binary decision but rather can include partial states or in-between states. For example, in some embodiments, and indication of the presence or absence of a disease or disease type can include clinical descriptors indicative of a pathology of one or more of the cells, of a portion of a slide image, or of the whole slide specimen (e.g., 80% abnormal cells, and the like). In some embodiments, the presence or absence of a disease or disease type can include a predicted survival rate, prognosis, prognostic interpretation, and the like. Prognoses and prognostic interpretations can include estimations of survival rate and survival time, estimations of treatment duration, estimations of timing for follow-up monitoring, and the like. In some embodiments, the presence or absence of a disease or disease type can include a prediction of human annotations for cytology analyses.

In some embodiments, the identification of important cells from stage 194a can be used in the processing at stage 194b. For example, the processing at stage 194b may include only the processing of the array of features scores for the cells identified as important. As another examples, the processing at stage 194b may include giving a predetermined weight to the array of features scores for the cells identified as important while still also processing the array for cells not identified as important.

In some embodiments, the system can provide an output (via, e.g., a graphical user interface (GUI) 235 as in FIG. 2), as at stage 199b, indicative of the presence or absence of a disease or disease type. In some embodiments, the output can provide textual, graphical, or numeric representation of the determined presence or absence of a disease or disease type. In some embodiments, the output can include photographic representation of cells or portions of the slide image (e.g., images of cells determined to be important, images of most likely diseased and most-likely non-diseased cell, images of an average sampling of the slide image, etc.) and/or the summary statistics for one or more feature scores. In some embodiments, the output can include an image of the whole slide, portion of slide, or artificial compiled image of cells, gallery of cells, and the like, overlaid with visual representations indicative of the presence or absence of a disease or disease type or highlighting of cells in the image used or determined to be important in the determination of the presence or absence of a disease or disease type. In some embodiments, the output can include one or more images of one or more important cells. In some embodiments, the output can include a gallery of images or a compiled virtual slide image of important cells. In some embodiments, the output indicative of the presence or absence of a disease or disease type can be used by a pathologist or other clinician or professional to determine a clinical diagnosis or final indication of the presence or absence of a disease or disease type. In some embodiments, the output indicative of the presence or absence of a disease or disease type can be used by a pathologist or other clinician or professional to prescribe a treatment or other tests deemed necessary or useful in determining a clinical diagnosis or indication of the presence or absence of a disease or disease type. In some embodiments, the output indicative of the presence or absence of a disease or disease type can be used by a non-clinician to provide a clinical diagnosis, without the involvement of a clinician, to a subject. Other optional embodiments are further described herein.

Figure 3:
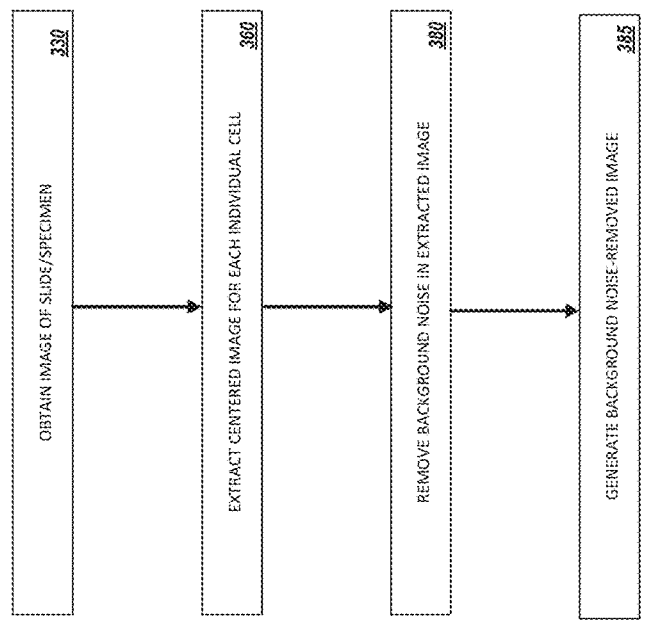
FIG. 3 is a flow chart of an exemplary method for improving digital image interpretation.

It has surprisingly been found that machine-based interpretation of a digital image of a specimen slide can be improved by isolating and extracting images of individual cells from within the whole slide image or image of a portion of the whole slide. Referring to FIG. 3, a method of improving image-based cell identification, classification, or analysis of one or more individual cells can include obtaining an image of a specimen slide, as at stage 330, and extracting, as at stage 360, for each of the one or more individual cells, an extracted image of the individual cell, wherein the cell is centered on the extracted image. The extracted image can then be processed, interpreted or analyzed according to methods described herein. In some embodiments, extraction of the centered image can include extracting an image of an individual cell by identifying the pixels that comprise the cell or the nucleus of the cell, determining the minimum and maximum height and width limits of those pixels, and outputting a new image that is a subset of the original image including only the pixels within those limits. In some embodiments, extraction of the centered image can include extracting an image of an individual cell by identifying the center of the pixels that comprise the cell or the nucleus of the cell, determining the coordinates of the box that is formed by subtracting or adding a fixed number of pixels to the cell center coordinates, and outputting a new image that is a subset of the original image that includes only the pixels within those coordinates. In some embodiments, extraction of the centered image can include identifying a particular cell or cell type to be extracted. For example, the whole slide image can first be processed using a cell classifier (for example, a known off-the shelf cell classifier algorithm) to determine cells of one or more types within the image. The spatial coordinates of the desired cell types can be determined and the extraction can then be conducted.

In some embodiments, an extracted image can have a size of from about 100 to 200 pixels by about 100 to 200 pixels. In some embodiments, a whole slide image can have a size of from about 80,000 pixels to about 1,000,000 pixels by about 80,000 pixels to about 1,000,000 pixels. In some embodiments, an extracted image can have a size of from about 0.0001% to about 0.005% of the size of the whole slide image.

Extracted images can optionally be further processed to further improve image-based cell identification, classification, or analysis of one or more individual cells. It has been surprisingly discovered that removing background noise in the extracted image, as at stage 380 of FIG. 3, in the extracted images of individual cells can significantly improve image-based cell identification, classification, or analysis of one or more individual cells in the slide image. For example, it has surprisingly been found that segmentation, or cutting out "background" around single cell images can improve the ability of machine learning classifiers to predict human annotations for cytology. In some embodiments, removing the background noise can include generating a new image for each extracted image using a watershed algorithm. In some embodiments, removing the background noise can include identifying the cell at the center of the extracted image and replacing all pixels outside the cell with a single color. For example, after detecting single cells in the whole slide image, small images centered on these cell detections can be extracted, as in step 360 of FIG. 3. Next, in stage 380, a watershed algorithm can be applied to identify the cells present. Another algorithm can be applied to identify only the cell at the center of the image. All pixels outside this detected cell can then be replaced with a single color (e.g., white), effectively removing the background from the image and leaving only the cell. This process can surprisingly improve not only the accuracy of feature classifiers, but also improve the whole slide level classification.

In some embodiments, a background noise-removed extracted image of a cell can be generated at stage 385, for use in any of the interpretation, analyses, classification, diagnostic, prognostic, and other methods described herein. For example, in some embodiments of the methods described herein, cell masking with a watershed algorithm can occur prior to the deep learning processes used in the slide image interpretation methods described herein.

It has surprisingly been found that cell cluster analysis can improve the accuracy of feature classifiers and/or the whole slide level classification. Thus in some embodiments, the methods can further include cell cluster analysis. Cell cluster analysis can include cell-type cluster analysis, true cell cluster analysis, and combinations thereof.

In some embodiments, cell-type cluster analysis can be used. Cell-type clusters are mathematical clusters of cells, such as groups of cells mathematically gathered around a particular value. The cell-type clusters can be determined with respect to one or more feature scores and can include a group of cells sharing more similar feature scores to each other than to those in other groups. Metrics from cell-type clusters, or clusters of cellular features, can be used as inputs for whole slide classification. In some embodiments, clustering the morphological characteristics of individual cells and then measuring the distances between cluster centers for a whole slide image can provide additional generalizable signal for predicting whole slide-level diagnoses. For example, after performing cell detection and optionally extracting small images centered on individual cells, a series of metrics can be generated from the image or each extracted image using both traditional computer vision methods and deep learning classifiers. In some embodiments, the metrics can directly be used as features for predicting the whole slide determination (e.g., determination of the presence or absence of a disease or disease type, determination of a clinical diagnosis, determination of important diagnostic cells). However, in some embodiments, the cell-type clusters can be used as additional features for predicting the whole slide determination. An exemplary process can include extracting signal from groupings of cells based on cellular or cytologic features. As an example, first, an unsupervised method such as gaussian mixture models or k-means can be applied to cluster all the cells on a slide. Next various metrics can be calculated for these clusters such as the distance between clusters (e.g., using a Mahalanobis metric) and the proportion of cells in each group. In some embodiments, a distance can be calculated for each cell classified within the cell-type cluster. These metrics can then be provided to the downstream algorithm for whole slide classification/determination.

Figure 4:
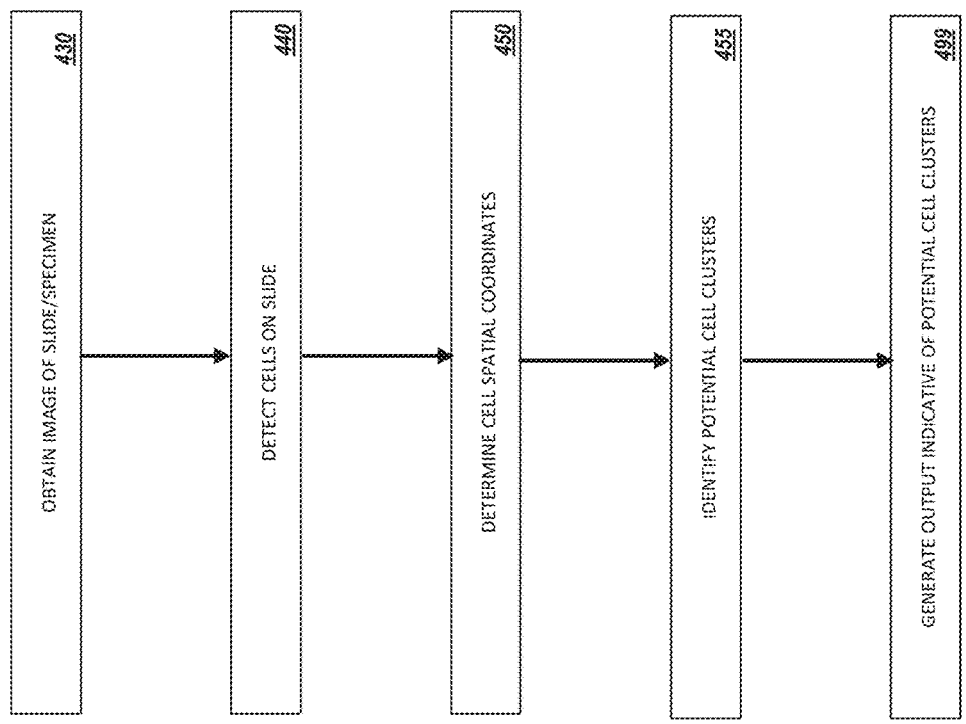
FIG. 4 is a flow chart of an exemplary method for identifying true cell clusters in a two-dimensional digital image.

In some embodiments, it has surprisingly been found that true cell cluster analysis can be beneficial in improving accuracy of the methods described herein. A "true cell cluster" refers to a group of cells in spatial proximity when measured by the system and that likely naturally originated in spatial proximity within the subject and/or specimen. True cell clusters can, in some embodiments, include cells arranged in or derived from a tumor or portion of a tumor. Clusters of attached cells originating from the same location in the body can often be indicative of low-grade neoplasia. For example, the cytological hallmark of low-grade urothelial neoplasia (LGUN) is one or more clusters of cells that exhibit a fibrovascular core. Many LGUN cases are missed, however, as the fibrovascular core is a three-dimensional feature and cytology slides are inherently two-dimensional. It has surprisingly been found that true cell clusters can be detected from these two-dimensional images using deep learning. A method described herein for detection of true cell clusters in cytological specimens is illustrated in FIG. 4. In some embodiments, the method generally includes first obtaining an image of a specimen slide, as in stage 430, detecting cells in the whole slide image, as in stage 440. Next, the spatial coordinates of the cells are determined, as in stage 450. For example, in some embodiments, the spatial coordinates can be determined by to a clustering algorithm (e.g., DBSCAN) to detect and identify potential true cell clusters, as in stage 455. In some embodiments, several rules (e.g. mean cell degradation below a threshold value) are applied to exclude artificial/fake clusters early in the process. The potential clusters, can in some embodiments, then be passed to a deep learning-based classifier that is trained on either human annotations of true clusters, or alternatively, weakly trained on the whole slide-level label (negative vs low-grade cancer) to identify true cell clusters. Finally, generating an output indicative of potential true cell clusters or true cell clusters, as in stage 499. In some embodiments, identifying potential true cell clusters or true cell clusters, as in stage 455, can include spatially clustering the cells, then classifying for potential true cell clusters using deep learning with human annotations or whole slide labels. In some embodiments, the output can include textual, graphical, numeric, or photographic representation of the true cell clusters or potential true cell clusters. In some embodiments, the output can be entered into the whole slide classifier as an additional feature to provide a whole slide determination such as a determinations of the presence or absence of a disease or disease type.

Figure 5:
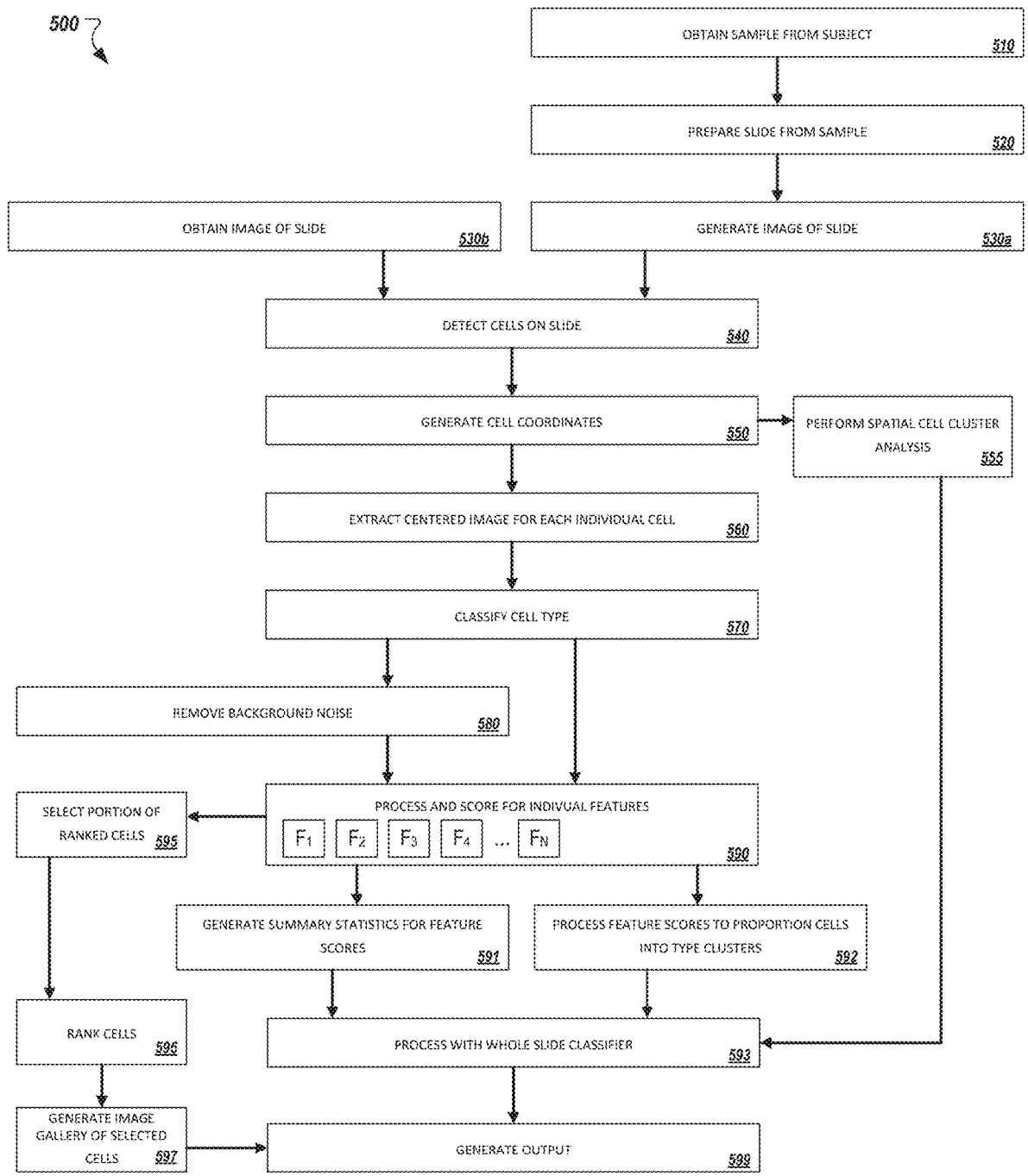
FIG. 5 is a flow chart of an exemplary method for interpreting a digital image of a slide or specimen.

In some embodiments, advanced interpretation methods can be used that combine two or more of the methods described herein. For example, as shown in FIG. 5, a method optionally combining two or more methods including image extraction, removal of background noise, cell type classification, feature scoring, cell-type cluster analysis, true cell cluster analysis identification of important or ranked cells, whole slide classification, and multiple outputs can be used. First, a digital image can be obtained at stage 530a or 530b. The image obtained at stage 530s can be obtained first by obtaining a specimen sample from a subject at stage 510. Next, at stage 520, a slide can be prepared from the specimen sample, including any desired sample processing processes. At stage 530a, an image can be generated, e.g., using a digital slide scanner or a digital camera. The image obtained at stage 530b can be an existing image. At stage 540, the cells on the whole slide image can be detected. At stage 550, spatial coordinates can be generated for each detected cell as described herein. Optionally, true cell cluster analysis as described herein can be performed using spatial cell cluster analysis at stage 555. After generating the cell coordinates, at stage 560, an extracted image can be produced for each individual identified cell, wherein the extracted image is centered on the cell. Next, at stage 570, the individual extracted images can be processed in a cell type classifier (e.g., an off-the shelf algorithm for determining cell type, such as, e.g., urothelial cells) to classify the cell type. In some embodiments, all the individual images, regardless of cell type can be further processed in the system. In other embodiments, one or more specific cell types may be selected for processing and the images for the selected cells will be extracted for use in the further processing. Optionally, background noise can be removed from the extracted images at stage 580 (e.g., using a watershed method), as described herein. Notably, stage 580 can optionally occur before or after stage 570, depending on the desired analysis. Next a feature vector can be identified and the system can process the extracted images and score each feature (e.g., $F_1$, $F_2$, $F_3$ . . . , $F_N$). Next the system can optionally proceed to any of stages 595, 591, or 592, or combinations thereof. At stage 595, the feature scores can be processed to rank cells, and a portion of the cells can be selected based on the ranking. The selected cell images can optionally be further ranked at stage 596 (e.g., for an output that includes a ranking relevant to a clinician or other professional reviewing the ranking), and one or more outputs indicative of the selected and/or ranked cell images can be generated at stage 597, such as an image gallery of selected cells and/or a visual representation of their ranking. The output can be displayed, e.g., on a GUI for review by a clinician or other professional. At stage 591, an array of feature scores can be processed to generate a metric, such as summary statistics of the feature scores. The summary statistics can include, without limitation, mean, median, standard deviation, variance, kurtosis, or skew, histograms, principal components analysis, or other dimensionality reduction methods, and combinations thereof. At stage 592, the array of feature scores can be processed by the system to proportion the cells into cell type cluster as described herein. The summary statistics generated from stage 591, the cell type cluster information generated from stage 592, or a combination thereof, can be processed with the whole slide classifier in stage 593 to determine, e.g., the presence or absence of a disease or disease type. Optionally, the true cell cluster analysis from stage 555 can also be processed with the whole slide classifier in stage 593. Finally, one or more outputs can be generated at stage 599, e.g., on a GUI, an interactive GUI, printed onto paper, etc. The outputs can include, without limitation, an output indicative of the presence or absence of a disease or disease type, images of one or more cells, a cell gallery or virtual slide, visual representations of various parameters of interest according to the disease or condition being analyzed, etc.

Figure 6:
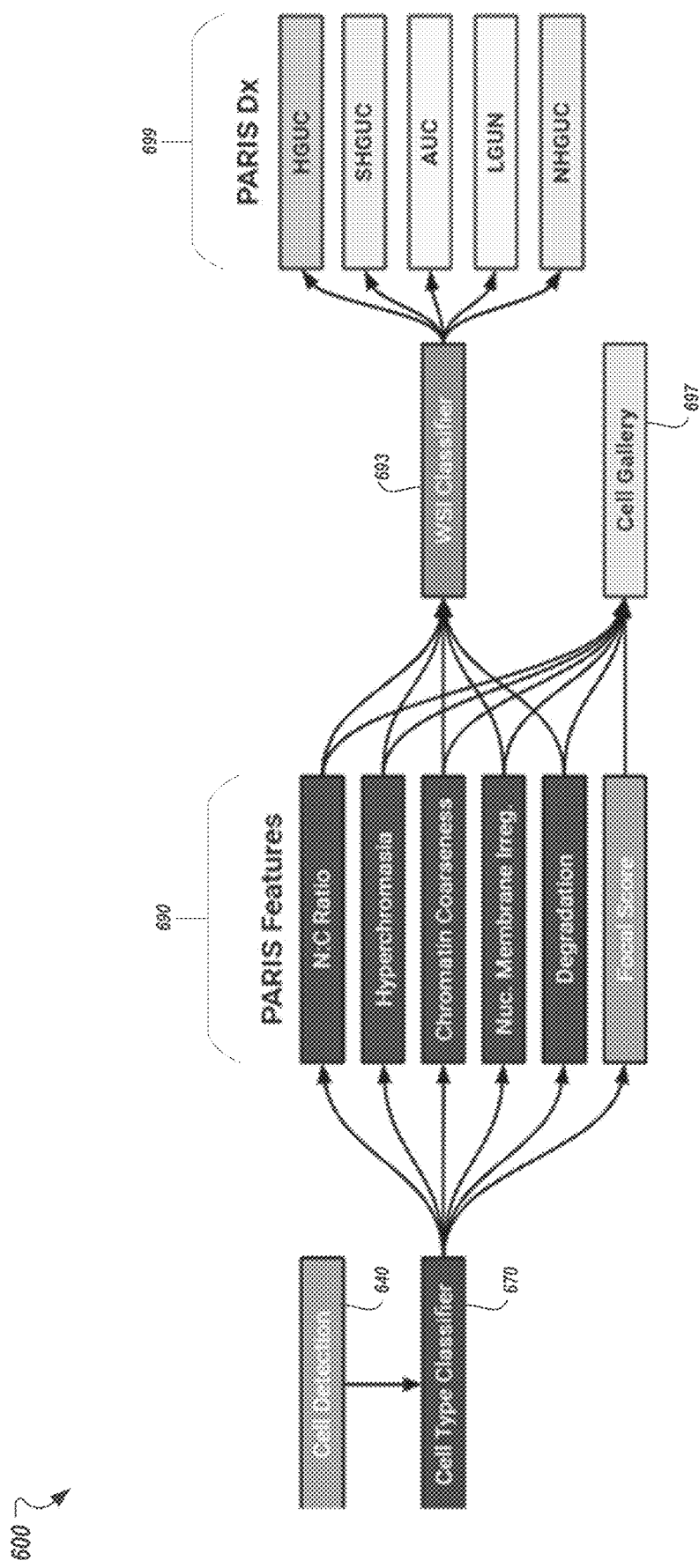
FIG. 6 is a flow chart of an exemplary method for interpreting a digital image of a slide or specimen.

Referring to FIG. 6, an exemplary method for interpreting a digital image of a slide or specimen is shown for the specific analysis of urinary cytology, which can be useful for evaluating urinary infections and cancers such as bladder cancer. After obtaining an image of a specimen slide, such as a slide prepared from a urine specimen, cells in the image are detected at stage 640. Next, each cell is evaluated by a cell classifier (e.g., a urothelial cell classifier) at stage 670. Urothelial cells are then evaluated by machine learning algorithms trained to score the cells, at stage 690, according to each clinical reporting criteria (e.g. PARIS reporting criteria), as well as degradation and focus. Next, at stage 693, whole-specimen interpretation classifier uses a statistical summary of the characteristics of urothelial cells to determine and output the interpretation, shown at stage 699, of the entire specimen, such as the presence or absence of a disease or disease type. In some embodiments, the disease or disease type can be selected from the group consisting of high grade urothelial carcinoma, suspicious for high grade urothelial carcinoma, low grade urothelial neoplasia, atypical urothelial cells, and negative for high grade urothelial carcinoma. Optionally, at stage 697, a cell gallery output can be generated based on the scores determined at stage 690. The cell gallery of stage 697 can be used in conjunction with the output at stage 699 by a clinician to verify the machine's clinical diagnosis, and/or make a final clinical diagnosis.

In some embodiments, the specimen or image can include a cellular specimen, such as a cytology specimen. In some embodiments, the cellular specimen can be an unprocessed specimen taken directly from a subject. In some embodiments, the specimen can be processed in some way, such as using dyes, chemicals, or by purification techniques. In some embodiments, aggregate specimens may be prepared from one or more specimens taken from the same subject or multiple subjects. In some embodiments, the specimen can include a tissue specimen, such as a histology specimen. In some embodiments, a specimen or image can include a portion of a histology image. In some embodiments, a specimen or image can include a tissue that contains a tumor. In some embodiments, tissue specimens, including tumor specimens can be evaluated using the true cell cluster analyses described herein.

Various diseases, conditions, and biological processes can be evaluated using the systems, methods, devices, and other techniques described herein. For example, without limitation, the systems, methods, devices, and other techniques described herein can be useful in evaluating cancers, infections, tissue injuries, cellular abnormalities, aging processes, recovery processes, and the like.

In some embodiments, the systems, methods, devices, and other techniques described herein can be used in methods of diagnosis, in a subject, a disease or condition. Such diagnostic methods can include determining the presence or absence of a disease or disease type in a subject, based on the subject's specimen using the systems, methods, devices, or other techniques described herein. In some embodiments, a method of diagnosing can include diagnosing, in a subject, a condition selected from the group consisting of high grade urothelial carcinoma, suspicious for high grade urothelial carcinoma, low grade urothelial neoplasia, atypical urothelial cells, and negative for high grade urothelial carcinoma including determining the presence or absence of a disease or disease type using the systems, methods, devices, or other techniques described herein.

In some embodiments, the systems, methods, devices, or other techniques described herein can be useful in methods of evaluating the effectiveness of a cancer intervention measure in a subject having or at risk for developing a cancer. Subjects considered at risk for developing cancer can include, e.g., individuals exposed to carcinogens, e.g., by consumption (e.g., by inhalation and/or ingestion), at levels that have been shown statistically to promote cancer in susceptible individuals. Also included are individuals at risk due to exposure to ultraviolet radiation, or their environment, occupation, and/or heredity, as well as those who show signs of a precancerous condition such as polyps. Similarly, individuals identified as being in very early stages of pre-cancer or cancer or development of metastases (i.e., only one or a few aberrant cells are present in the individual's body or at a particular site in an individual's tissue) can be consider at risk individuals that can be monitored.

Evaluative methods can include determining the existence of cancerous or precancerous cells or tissue using the systems, methods, devices, or other techniques described herein; applying at least one intervention measure that is commensurate with the treatment or prevention of the cancer; and determining the effectiveness of the intervention measure. In some embodiments, the effectiveness of the intervention measure can be determined by repeat or continuous monitoring based on standard diagnostic methods known for the particular cancer type. In some embodiments, the effectiveness of the intervention measure can be determined by repeat or continuous interpretation of specimens from the subject using the systems, methods, devices, or other techniques described herein. In some embodiments, the intervention method can be surgery, chemotherapy (including chemotherapeutic drugs such as doxorubicin), radiation therapy, immunotherapy, hormone therapy, stem cell transplantation, diet intervention, lifestyle intervention, and combinations thereof.

In some embodiments, the diagnosis, prognosis, or evaluation of treatment can be for any disease that can be evaluated at a cellular or tissue level, including, for example, a neoplasm (benign or malignant cancer); a neurological disease (e.g., a neurodegenerative disease or cognitive disease such as Alzheimer's, Parkinson's etc.), a degenerative disease, a cardiovascular disease, an ophthalmologic disease, a skeletal disease, a metabolic disease, an autoimmune disease (e.g. Crohn's, rheumatoid arthritis, all types of arthritis, etc.), inflammatory disease, graft-vs-host disease; hematological disease, congenital or hereditary disease, infectious diseases (e.g., HIV, hepatitis, malaria), as well as reactive processes and iatrogenic conditions.

Non-limiting examples of cancers include: acute lymphoblastic leukemia (ALL), acute myeloid leukemia (AML), cancer in adolescents, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CIVIL), chronic myeloproliferative neoplasms, colon cancer, colorectal cancer, craniopharyngioma, cutaneous T-cell lymphoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, glioblastoma, hairy cell tumor, hairy cell leukemia, head and neck cancer, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteosarcoma, melanoma, Merkel cell carcinoma, mesothelioma, metastatic squamous neck cancer, midline tract carcinoma, mouth cancer, multiple endocrine neoplasia syndromes, multiple myeloma, mycosis fungoides, myelodysplastic syndromes, myelodysplastic/myeloproliferative neoplasms, myelogenous leukemia, myeloid leukemia, multiple myeloma, myeloproliferative neoplasms, nasal cavity and paranasal sinus cancer, nasopharyngeal cancer, neuroblastoma, non-Hodgkin's lymphoma, non-small cell lung cancer, oral cancer, oral cavity cancer, lip cancer, oropharyngeal cancer, osteosarcoma, ovarian cancer, pancreatic cancer, papillomatosis, paraganglioma, paranasal sinus and nasal cavity cancer, parathyroid cancer, penile cancer, pharyngeal cancer, pheochromocytoma, pituitary cancer, plasma cell neoplasm, pleuropulmonary blastoma, pregnancy and breast cancer, primary central nervous system lymphoma, primary peritoneal cancer, prostate cancer, rectal cancer, renal cell cancer, retinoblastoma, rhabdomyosarcoma, salivary gland cancer, sarcoma, Sezary syndrome, skin cancer, small cell lung cancer, small intestine cancer, soft tissue sarcoma, a solid cancer, squamous cell carcinoma, squamous neck cancer, stomach cancer, T-cell lymphoma, testicular cancer, throat cancer, thymoma and thymic carcinoma, thyroid cancer, transitional cell cancer of the renal pelvis and ureter, unknown primary carcinoma, urethral cancer, uterine cancer, uterine sarcoma, vaginal cancer, vulvar cancer, and Wilms' tumor. In some embodiments, the disease can be thyroid cancer, lung cancer, brain cancer, kidney cancer, pancreatic cancer, breast cancer, biliary cancer, cervical cancer, or liver cancer. In some embodiments, a cancer may be primary (e.g., a primary tumor) or metastatic (e.g., a metastatic tumor).

Non-limiting types of infections include viral infections, bacterial infections, fungal infections, parasitic infections, and protozoal infections. Non-limiting examples of infections include *Acinetobacter* infections, Actinomycosis, African sleeping sickness (African trypanosotniasis), AIDS (Acquired immunodeficiency syndrome), Amebiasis, Anaplasmosis, Angiostrongyliasis, Anisakiasis, Anthrax. *Arcanobacterium haemolyticum* infection, Argentine hemorrhagic fever, Ascariasis, Aspergillosis, Astrovirus infection, Babesiosis, *Bacillus cereus* infection, Bacterial pneumonia, Bacterial vaginosis, *Bacteroides* infection, Balantidiasis, Bartonellosis, *Baylisascaris* infection, BK virus infection, Black piedra, Blastocystosis. Blastomycosis, Bolivian hemorrhagic fever, Botulism (and Infant botulism), Brazilian hemorrhagic fever, Brucellosis, Bubonic plague, *Burkholderia* infection, Buruli ulcer, Calicivirus infection (Norovirus and Sapovirus), Campylobacteriosis, Candidiasis (Moniliasis; Thrush), Capillariasis, Carrion's disease, Cat-scratch disease, Cellulitis, Chagas Disease (American trypanosomiasis), Chancroid, Chickenpox, Chikungunya, *Chlamydia, Chlamydophila pneumoniae* c infection (Taiwan acute respiratory agent or TWAR), Cholera, Chromoblastomycosis, Chytridiomycosis, Clonorchiasis, *Clostridium difficile* colitis, Coccidioidomycosis, Colorado tick fever (CTF), Common cold (Acute viral rhinopharyngitis; Acute coryza), Creutzfeldt-Jakob disease (CJD), Crimean-Congo hemorrhagic fever (CCHF), Cryptococcosis, Cryptosporidiosis, Cutaneous larva migrans (CLM), Cyclosporiasis, Cysticercosis, Cytomegalovirus infection, Dengue fever, Desmodesmus infection, Dientamoebiasis, Diphtheria, Diphyllobothriasis, Dracunculiasis, Ebola hemorrhagic fever, Echinococcosis, Ehrlichiosis, Enterobiasis (Pinworm infection), *Enterococcus* infection, Enterovirus infection, Epidemic typhus, Erythema infectiosum (Fifth disease), Exanthem subitum (Sixth disease), Fasciolasis, Fasciolopsiasis, Fatal familial insomnia (FFL), Filariasis, Food poisoning by *Clostridium perfringens*, Free-living amebic infection, *Fusobacterium* infection, Gas gangrene (Clostridial myonecrosis), Geotrichosis, Gerstmann-Straussler-Scheinker syndrome (GSS), Giardiasis, Glanders, Gnathostomiasis, Gonorrhea, Granuloma inguinale (Donovanosis), Group A streptococcal infection, Group B streptococcal infection, *Haemophilus* infection, Hand, foot and mouth disease (HFMD), Hantavirus Pulmonary Syndrome (HPS), Heartland virus disease, Helicobacterpylori infection, Hemolytic-uremic syndrome (HUS), Hemorrhagic fever with renal syndrome (HFRS), Hepatitis A, Hepatitis B, Hepatitis C, Hepatitis D, Hepatitis E, Herpes simplex, Histoplasmosis, Hookworm infection, Human bocavirus infection, Human ewingii ehrlichiosis, Human granulocytic anaplasmosis (HGA), Human immnunodeficiency virus (HIV) infection, Human metapneumovirus infection, Human monocytic ehrlichiosis, Human papillomavirus (HPV) infection, Human parainfluenza virus infection, Hymenolepiasis, Epstein-Barr virus infectious mononucleosis (Mono), Influenza (flu), Isosporiasis, Kawasaki disease, Keratitis, Kingella kingae infection, Kuru, Lassa fever, Legionellosis (Legionnaires' disease), Legionellosis (Pontiac fever), Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever (MHF), Measles, Middle East respiratory syndrome (MERS), Melioidosis (Whitmore's disease), Meningitis, Meningococcal disease, Metagonimiasis, Microsporidiosis, Molluscum contagiosum (MC), Monkeypox, Mumps, Murine typhus (Endemic typhus), *Mycoplasma* pneumonia, *Mycoplasma genitalium* infection, Mycetoma (disambiguation), Myiasis, Neonatal conjunctivitis (Ophthalmia neonatorum), Norovirus (children and babies), (New) Variant Creutzfeldt-Jakob disease (vCJD, nvCJD), Nocardiosis, Onchocerciasis (River blindness), Opisthorchiasis, Paracoccidioidomycosis (South American blastomycosis), Paragonimiasis, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Plague, Pneumococcal infection, Pneumocystis pneumonia (PCP), Pneumonia, Poliomyelitis, Prevotella infection, Primary amoebic meningoencephalitis (PAM), prion diseases. Progressive multifocal leukoencephalopathy, Psittacosis, Q fever, Rabies, Relapsing fever, Respiratory syncytial virus infection, Rhinosporidiosis, Rhinovirus infection, Rickettsial infection, Rickettsialpox, Rift Valley fever (RVF), Rocky Mountain spotted fever (RMSF), Rotavirus infection, Rubella, *Salmonellosis*, SARS (Severe Acute Respiratory Syndrome), Scabies, Scarlet fever, Schistosomiasis, Sepsis, Shigellosis (Bacillary dysentery), Shingles (Herpes zoster), Smallpox (Variola), Sporotrichosis, Staphylococcal food poisoning, Staphylococcal infection, Strongyloidiasis, Subacute sclerosing panencephalitis, Syphilis, Taeniasis, Tetanus (Lockjaw), Tinea barbae (Barber's itch), Tinea capitis (Ringworm of the Scalp), Tinea corporis (Ringworm of the Body), Tinea cruris (Jock itch), Tinea manum (Ringworm of the Hand), Tinea nigra, Tinea pedis (Athlete's foot), Tinea unguium (Onychomycosis), Tinea versicolor (Pityriasis versicolor). Toxocariasis (Ocular Larva Migrans (OLM)), Toxocariasis (Visceral Larva Migrans (VLM)), Toxoplasmosis, Trachoma, Trichinosis, Trichomoniasis, Trichuriasis (Whipworm infection), Tuberculosis, Tularemia, Typhoid fever, Typhus fever, *Ureaplasma urealyticum* infection, Valley fever, Venezuelan equine encephalitis, Venezuelan hemorrhagic fever, *Vibrio vulnificus* infection, *Vibrio parahaemolyticus* enteritis, Viral pneumonia, West Nile Fever, White piedra (Tinea blanca), *Yersinia pseudotuberculosis* infection, Yersiniosis, Yellow fever, Zika fever, and Zygomycosis.

Non-limiting examples of autoimmune diseases include Achalasia, Addison's disease, Adult Still's disease, Agammaglobulinemia, Alopecia areata, Amyloidosis, Ankylosing spondylitis, Anti-GBM/Anti-TBM nephritis, Antiphospholipid syndrome, Autoimmune angioedema, Autoimmune dysautonomia, Autoimmune encephalomyelitis, Autoimmune hepatitis, Autoimmune inner ear disease (MED), Autoimmune myocarditis, Autoimmune oophoritis, Autoimmune orchitis, Autoimmune pancreatitis, Autoimmune retinopathy, Axonal & neuronal neuropathy (AMAN), Baló disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Diabetes (e.g., Type I diabetes, type II diabetes, gestational diabetes), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome—Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome (SPS), Subacute bacterial endocarditis (SBE), Susac's syndrome, Sympathetic ophthalmia (SO), Takayasu's arteritis, Temporal arteritis/Giant cell arteritis, Thrombocytopenic purpura (TTP), Tolosa-Hunt syndrome (THS), Transverse myelitis, Ulcerative colitis (UC), Undifferentiated connective tissue disease (UCTD), Uveitis, Vasculitis, Vitiligo, Vogt-Koyanagi-Harada Disease, and Wegener's granulomatosis (or Granulomatosis with Polyangiitis (GPA)).

Non-limiting examples of cellular abnormalities include dysplasia, neoplasia, degeneration, inflammation, scarring, apoptosis, and necrosis. Non-limiting examples of biological processes, including cellular and whole-body processes, include growth, proliferation, regeneration, maturation, differentiation, metaplasia, healing, aging, and death. As used herein, the term "subject" refers to any organism. For example, a subject can be a mammal, amphibian, fish, reptile, invertebrate, bird, plant, archaea, fungus, bacteria. In some embodiments, the subject is a mammal. In some embodiments, the subject may be a rodent (e.g., a mouse, a rat, a hamster, a guinea pig), a canine (e.g., a dog), a feline (e.g., a cat), an equine (e.g., a horse), an ovine, a bovine, a porcine, a primate, e.g., a simian (e.g., a monkey), an ape (e.g., a gorilla, a chimpanzee, an orangutan, a gibbon), or a human. In some embodiments of any of the methods described herein, the subject is between 0 and 120 years old (e.g., between birth and one month (e.g., a neonate), between one month and two years (e.g., an infant), between 2 years and 12 years (e.g., a child), between twelve years and sixteen years (e.g., an adolescent). In some embodiments of any of the methods described herein, the subject is not yet born, e.g., in utero. In some embodiments of any of the methods described herein, the subject is at least 1 month old (e.g., at least 2 years old, at least 12 years old, at least 16 years old, or at least 18 years old). Any of the methods described herein can be used to evaluate, diagnose, or monitor the treatment of a subject, e.g., a diseased subject (i.e., a subject with a disease, e.g., who has been diagnosed with a disease), or an asymptomatic subject (i.e., a subject who clinically presents as healthy, or who has not been diagnosed with a disease).

In some embodiments, the systems, method, devices, and other techniques described herein can be useful in diagnosing, or assisting in diagnosis of, various diseases and conditions. In some embodiments, automated systems described herein can provide a final diagnostic output (e.g., "high grade urothelial carcinoma") that can be used, without further human interpretation or assistance, as a clinical diagnosis of a subject. In some embodiments, the final diagnostic output (e.g., "high grade urothelial carcinoma") can be used to assist a clinician or other professional in determining a clinical diagnosis for a subject. In some embodiments, the systems, method, devices, and other techniques described herein can also be useful in determining or providing a prognosis for a disease, condition, treatment, or process.

For example, an automated system may indicate a specific diagnosis or prognosis, and the clinician may review that diagnosis or prognosis, then review the specimen and decide if the automated diagnosis or prognosis is appropriate. In some embodiments, the automated system can provide useful diagnostic or prognostic information to assist a clinician or other professional in determining a diagnosis or prognosis for the subject or specimen. For example, an automated system described herein can provide one or more outputs containing information useful to a diagnostician in diagnosing a subject or specimen. Exemplary output information useful in diagnosis or prognosis can include, without limitation, cell count, cell type count, identification of cells determined by an automated system to be important in clinical diagnosis of a selected disease or condition, microscope focus conditions, microscope focus quality, specimen or cell quality (e.g., whether or not a given cell, cell population, or specimen is degraded), disease type probability, disease type suggestion, disease grade suggestion, diagnosis, diagnosis subtype, disease stage, specimen adequacy, and specimen triage for ancillary testing. Combinations of these methods are also envisioned.

Figure 8A:
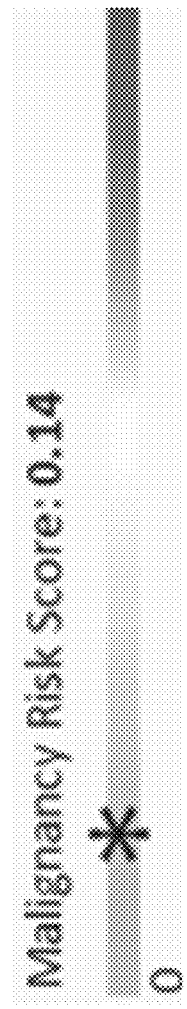
FIG. 8A is an exemplary visual output.

In some embodiments, visual outputs, interfaces, and/or graphical user interfaces are provided for displaying and interacting with information or diagnosis/prognosis determined from an automated system. In some embodiments, a visual interface can include an image of a whole specimen slide including biological cells, overlaid with a visual representation of a prediction score for each of one or more cells identified in the slide. In some embodiments, a visual representation of the prediction score can be a color. For example, a single color, such as blue, can indicate normal cells, while a different single color, such as orange, can indicate abnormal or suspect cells. In some embodiments, a visual representation of the prediction score can be an outline around one or more cells in the image. In some embodiments, a prediction score can provide a visual indication of an importance score for each identified cell based on the cell's importance in determining the presence or absence of a disease or disease type. In some embodiments, a prediction score can provide a visual indication of a point on a severity scale. The severity scale can be indicative of a severity of a disease or disease type. In some embodiments, a prediction score can provide a visual indication of an overall predicted malignancy for the whole slide, as depicted in visual output 803 of FIG. 8A. In some embodiments, a prediction score can provide a visual indication of a value of an individual cytomorphologic criteria feature score. In some embodiments, a prediction score can be a numerical value that specifies, or is used to compute at least one of a grayscale, a shading type, a color, and a second numerical value.

Figure 8B:
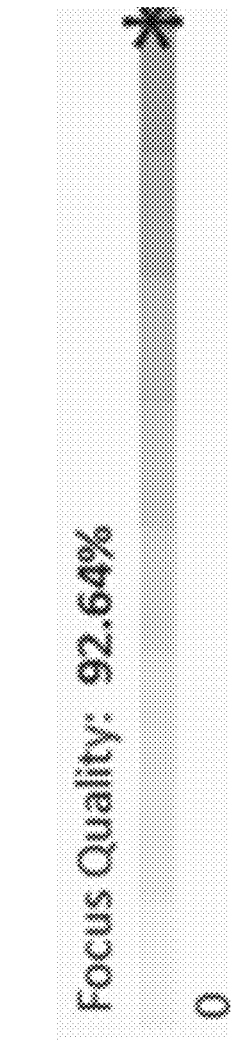
FIG. 8B is an exemplary visual output.
Figure 8C:
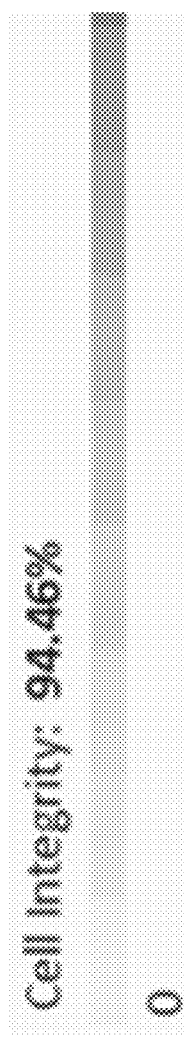
FIG. 8C is an exemplary visual output.

In some embodiments, image augmentation can optionally be included for further optimization of the system and methods. In some embodiments, visual outputs can provide information such as the quality of focus of the slide image, such as in the visual output 804 of FIG. 8B. Other information presented visually can include an indication of the cellular integrity, such as in visual output 805 of FIG. 8C. The cellular integrity can be determined for an individual cell, a selected group of cells, or the whole slide. In some embodiments, the cellular integrity indication can provide information about the quality of the sample, such as the degradation or age or handling of the sample. In some embodiments, the cell integrity can provide diagnostic information relating to the disease state of the cell.

Figure 7B:
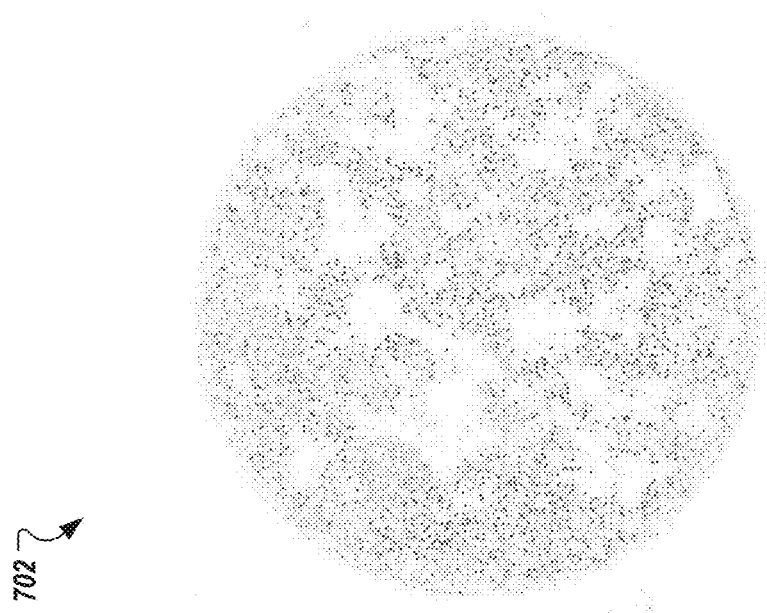
FIG. 7B is an exemplary visual output of a whole slide image of a sample positive for a certain disease or condition.
Figure 7A:
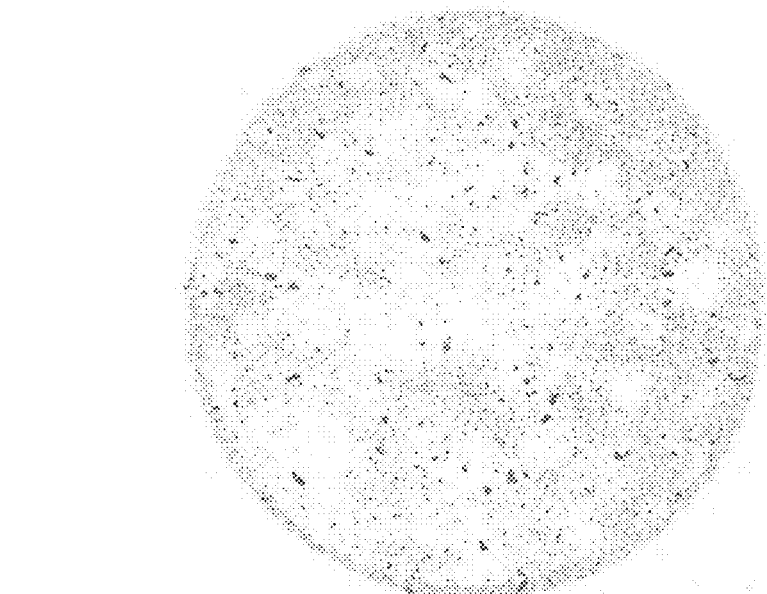
FIG. 7A is an exemplary visual output of a whole slide image of a sample negative for a certain disease or condition.

Referring to FIGS. 7A and 7B, visual interfaces showing whole slide images are shown. FIG. 7A exemplifies a whole slide image 701 for a specimen that is negative for a particular condition. FIG. 7B exemplifies a whole slide image 702 for a specimen that is positive for a particular condition. The cells in FIG. 7A and FIG. 7B appear in various shades of a single color, e.g., blue, the color being selected as representative of, for example, a lower or higher probability of disease, disease type, or abnormality. Some of the cells appear with a darker shade of the respective color (e.g., blue or red). In some embodiments, the darker shade can indicate cells which, for example, have been determined by the system to be most relevant for diagnostics, are determined to be most abnormal, are determined to provide the most information or most relevant information for the suspected disease or desired test, are determined to be adequate for analysis, are determined to be of good analytic quality, are determined to have no or little aberrations or artifacts, are determined to include a selected stain, are determined to be in the best visual focus, are determined to be well-preserved cells, and the like.

Figure 8D:
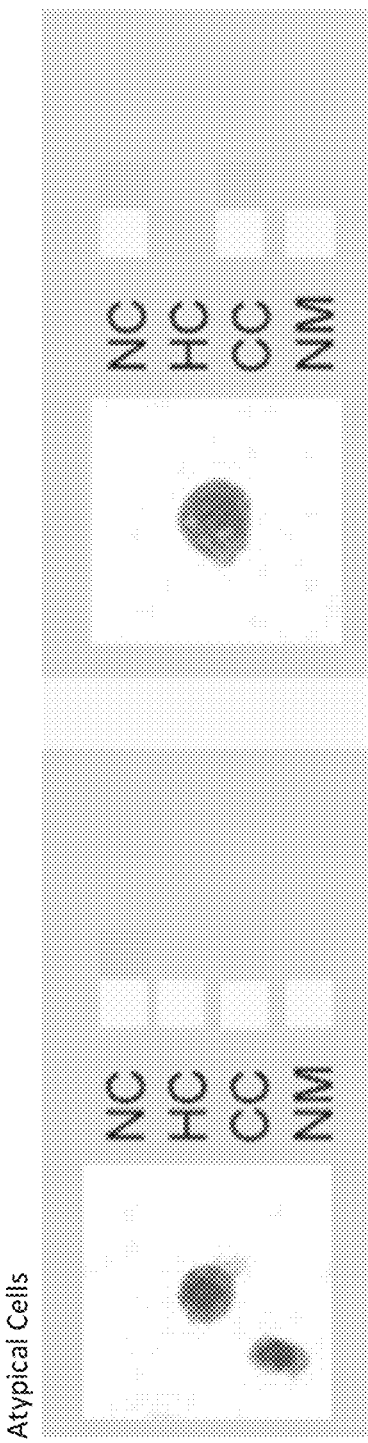
FIG. 8D is an exemplary visual output.

In some embodiments, a visual interface can comprise a collection of images. In some embodiments, each image can be of an individual cell and be extracted from a whole specimen slide image comprising a plurality of cells. In some embodiments, each image in the collection can comprise one or more scores or visual representations of scores corresponding to each of one or more cytomorphologic criteria features or diagnostic or prognostic estimations or determinations. For example, in some embodiments the collection can appear similar to the whole slide images in FIGS. 7A and 7B, but instead of depicting all cells in the whole slide, can depict a limited number of selected cells or tissue portions. The selected cells or tissue portions can be identified by the system according to parameters desired to be viewed, such as cells or portions having a particular feature score or set of scores above or below a predetermined threshold. For example, FIG. 8D shows a gallery 806 of atypical cells, as determined by the system.

In some embodiments, a visual interface can comprise a single composite image comprising a plurality of selected individual cell images extracted from a whole specimen slide image comprising a plurality of cells. In some embodiments, the selected cells can consist of cells identified as exceeding a predetermined threshold based on a presence or absence of a disease or disease type determined from a combination of individual cytomorphologic criteria feature scores. In some embodiments, each image in the collection can be an image of an individual true cell cluster identified by the system and extracted from a whole specimen slide image comprising a plurality of cells and true cell clusters. Each image can further comprise one or more scores corresponding to a presence or absence of a cellular or whole slide disease or disease type.

One advantage of the systems and methods described herein includes using the systems and methods to adapt the systems to produce an optimized composite cell image or gallery of cell images useful in determining a diagnosis or the presence or absence of a disease or disease type in a specimen. In some embodiments, a plurality of composite images or galleries can be produced to further train the system to optimize the number of cells required in the composite image or gallery to allow a clinician or a machine learning system to determine an accurate presence or absence of a disease or disease type. In some embodiments, a plurality of composite images or galleries can be produced to further train the system to optimize the selection of characteristics of cells chosen for inclusion in a composite image or cell gallery to allow a clinician or a machine learning system to determine an accurate diagnosis. In some embodiments, supervised training may be used to determine the number and characteristics of cells chosen for inclusion in a composite image or cell gallery to allow a clinician or a machine learning system to determine an accurate presence or absence of a disease or disease type. In some embodiments, a visual interface comprising a single composite image or a gallery of images useful in determining a diagnosis or the presence or absence of a disease or disease type in a specimen can include an input that allows a clinician or other professional to give feedback to the system as part of supervised learning.

In some embodiments, an output can include a visual interface to guide cytopathologist or histologist interpretation, or to assent to the system interpretation, by displaying specimen-derived information and incorporating cytopathologist feedback. In some embodiments, an output can include summary measurements such as the count and distribution of cells of a certain malignancy present. In some embodiments, an output can include a display of summary measurements of the specimen in comparison to other collected specimens with the same interpretation. In some embodiments, an output can include a summary image of the entire scanned specimen indicating each identified cell, using color to indicate the importance of each cell based on either overall predicted malignancy or individual clinical guideline features. In some embodiments, an output can include a gallery of cell images with scores for relevant features from clinical guidelines. In some embodiments, an output can include a gallery of cell cluster images with score indicating risk of low-grade neoplasia. In some embodiments, an output can include virtual slide displaying a selection of only the most relevant cells (e.g. urothelial cells when analyzing for bladder cancer).

In some embodiments, it can be important to ensure the information from the specimen is reduced into a form useful to the cytotechnologist or pathologist for diagnosis or validation of a diagnosis. The methods and systems described herein can produce visual outputs that are useful, accurate, and safe.

In some embodiments, methods are provided machine-only (e.g., automated system) interpretation of specimens. In some embodiments, methods are provided for joint human-machine interpretation of specimens. The visual outputs described above can be useful in the joint human-machine interpretation of specimens. In some embodiments, a method of joint human-machine interpretation of a specimen can include using any of the systems and methods described herein to review the specimen image via an automated system and provide one or more outputs, including, for example, textual outputs, numeric outputs, shaded or color visual representations, images, and the like, as well as combinations thereof. Then, the clinician or other professional can review the outputs of the system and make the final determination of diagnosis and/or prognosis. In some embodiments the In some embodiments, the systems, method, devices, and other techniques described herein can be used to monitor or predict the progression and rate of development of a disease, condition, or process. Prognostic outlooks that can be determined can include, without limitation, disease evolution (e.g., whether the condition will progress to a specific disease type) and timing of progression (e.g., disease progression rate, treatment duration expectancy, life expectancy, and the like). For example, in some embodiments, the systems, method, devices, and other techniques described herein can be used to predict the progression of various cancers. In some embodiments, whether a disease is terminal, and the duration of the disease or condition can be predicted. In some embodiments, treatment duration can be predicted. For example, the systems, method, devices, and other techniques described herein can be used to monitor and predict the duration required for a specific therapy, a cancer treatment, administration of an antibiotic or antiviral, or recommended recovery time following an injury, surgery, or elective surgery. In some embodiments, non-disease processes, such as cellular or whole organism aging, can be monitored and/or predicted.

In some embodiments, determining the presence or absence of a disease or disease type can be further based on one or more separate diagnostic tests performed on the subject, distinct from the slide image. In some embodiments, data from the one or more separate diagnostic tests can be included for processing in the whole slide classifier. In some embodiments, data from the one or more separate diagnostic tests can be used solely by a clinician or other professional validating the determination of the presence or absence of a disease or disease type output by the system, or in conjunction with an output from the system, such as a gallery of important diagnostic cells, and/or the system's determination of the presence or absence of a disease or disease type. In some embodiments, the one or more separate diagnostic tests are selected from the group consisting of subject imaging, subject sample imaging, a blood test, a urine test, a fine needle aspirate test, a sputum test, a lumbar puncture test, or a pap smear test. In some embodiments, the one or more separate diagnostic tests comprise fluorescent in situ hybridization.

In some embodiments, diagnostic performance of the systems and methods described herein using cytomorphologic training data, possibly augmented with histologic training data, can be improved over the performance of conventional diagnostic methods performed by cytopathologists using cytomorphic training data. For example, a diagnosis made or recommended by the systems and methods described herein using cytomorphologic data from a patient (e.g., an image of urothelial cells collected from a simply obtained and/or non-invasive urine sample), but not histologic data, can, in some embodiments, be more accurate than a conventional diagnosis by one or more cytopathologists. Even greater accuracy can be achieved with the use of histologic training data when available. For example, in one case in which the system is trained with the benefit of histological results, the system's performance when measured against histology results is better than that of cytopathologists (58.1% vs. 45.6% accuracy) examining the image (when also compared to histology results). In some embodiments, to improve the performance of the systems and methods described herein, an ensemble model can be used to train the systems on information from cytology as well as follow up histology diagnosis when available. For example, in some embodiments, two gradient boosting classifiers can be used for to train the systems based on (a) cases with just cytology diagnosis, and (b) cases where the histology diagnosis is present. The output of both of these models, as well as the slide-level features, can then be fed into a logistic regression model trained on the histology diagnoses through cross validation. In some embodiments, the accuracy of the systems and methods described herein can be greater than 50%, greater than 55%, greater than 58%, or more. In some embodiments, the accuracy of the systems and methods described herein can be at least 20%, at least 25%, or at least 28% more accurate than the average performance of human cytopathologists. In some embodiments, the accuracy of cytopathologists and/or the systems and methods described herein can be assessed using histologic results.

Figure 10:
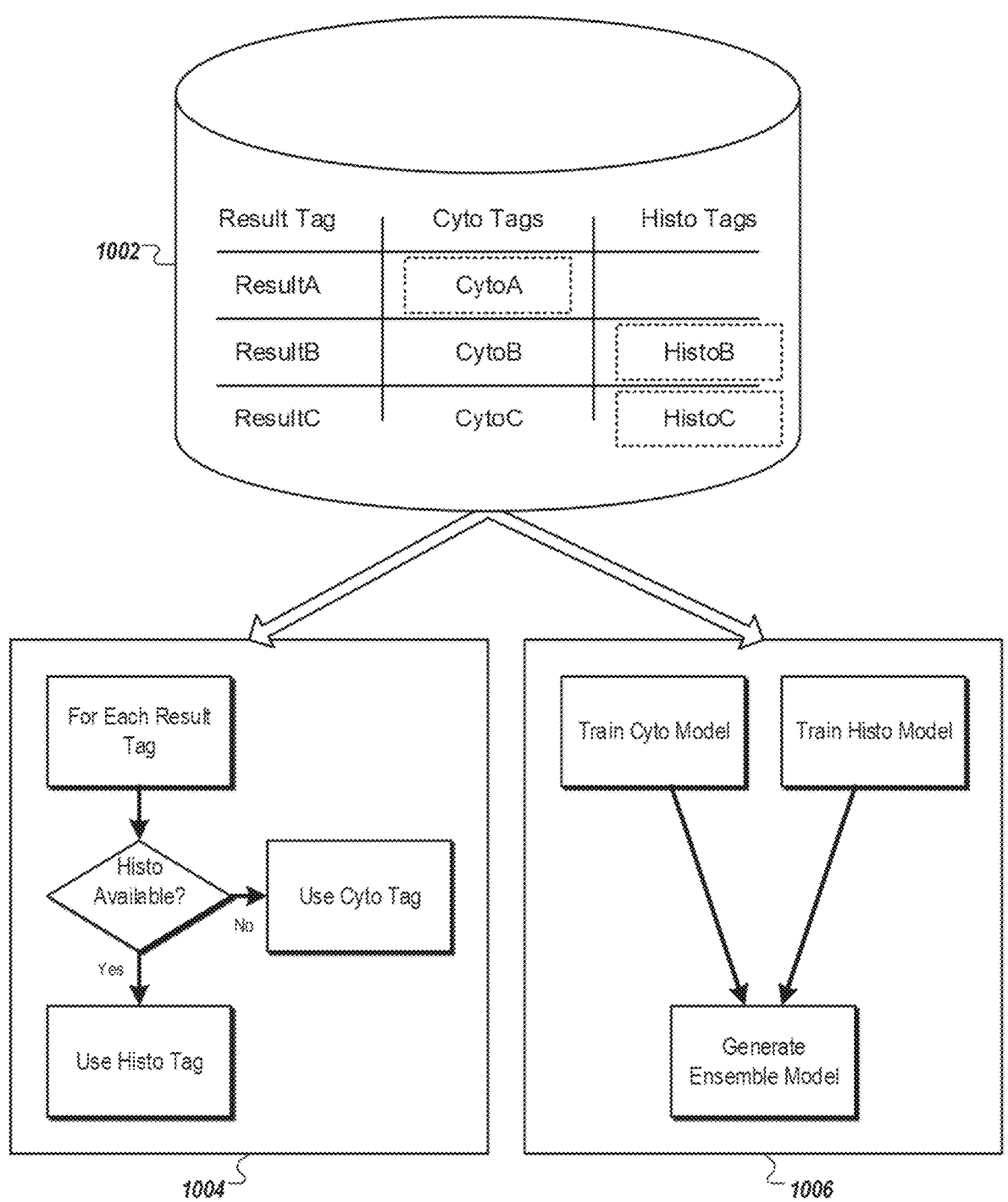
FIG. 10 is a block diagram of an example system that can be used to train classifiers that are useful for interpreting a digital image of a slide or specimen.

FIG. 10 is a block diagram of an example system that can be used to train classifiers that are useful for interpreting a digital image of a slide or specimen in some embodiments of the systems and methods described herein. A datastore 1002 can store data used to train classifiers that can be used as described in this document. The data in the datastore 1002 can include tags usable by one or more machine learning processes that generate classifiers that are capable of classifying digital images of a slide or specimen.

For example, the data in the datastore 1002 can include result tags that represent various conditions or pathologies that a slide or specimen should be classified as. These can include, for example, diseases carried by or indicated by cells in the specimen.

The data in the datastore 1002 can include feature tags for the associated result tags, including cytomorphologic tags generated via cytomorphologic analysis and/or histological tags generated by histological analysis. In some cases, some of the results may have both types of result tags, and in some cases, some of the results may only have one or the other type of result tags (e.g., some missing cytomorphologic tags, some missing histologic tags, or some of each missing).

In various machine learning processes, the cytomorphologic tags and the histologic tags can be used to train classifiers that classify data into a matching result tag. In scheme 1004, histologic tags are used if they are available, and if the histologic tags are not available, cytomorphologic tags are used. It will be appreciated that in an alternative example, cytomorphologic tags may be used if available, and histologic tags used only as a back-up if the histologic tags are not available.

In scheme 1006, a cytomorphologic model is trained and a histologic model is trained. Then, an ensemble model can be generated using the cytologic and histologic model together. For example, the cytomorphologic model and the histologic model may produce cytomorphologic confidence values and histologic confidence values correspondingly. The ensemble model may generate a final classification by aggregating these two confidence values. For example, for a model intended to be bias to high accuracy but low inclusivity (that is, one with few false positives at the cost of more false negatives) the ensemble model may return a classification if and only if both confidence values are above corresponding thresholds. For a model intended to be bias to high inclusivity but low accuracy (that is, one with few false negatives at the cost of more false positives) the ensemble model may return a classification if either confidence value is above a corresponding threshold, or if the sum of both confidence values is above a threshold value. As will be understood, different ensemble models may be useful for different purposes. A model with high inclusivity but low accuracy may be appropriate for a screening of the general population intended to direct patients to follow-up testing. On the other hand, a model with high accuracy but low inclusivity may be used as part of a chain of test conforming to Bayesian logic that are intended to identify particularly rare diagnoses of patients.

The systems, method, devices, and other techniques described herein are readily adaptable to changing knowledge and standards. For example, cytological and histological clinical standards (e.g., PARIS for urinary cytology, Bethesda for cervical cytology, and the like) can change over time as changes in evaluative technology and collective understanding occur. One skilled in the art will recognize that the systems, method, devices, and other techniques described herein are advantageously readily adaptable to such changes. Further, such adaptations can advantageously have limited training requirements as compared to training human clinicians or other professionals.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory program carrier for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer storage medium can be a machine-readable storage device, a machine-readable storage substrate, a random or serial access memory device, or a combination of one or more of them. The computer storage medium is not, however, a propagated signal.

The term "processing system" can include a data processing apparatus encompasses all kinds of apparatus, devices, and machines for processing data, including by way of example a programmable processor, a computer, or multiple processors or computers. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a standalone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program include, by way of example, can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device such as a GUI, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Some embodiments described herein can include, without limitation:

Embodiment 1

A method, comprising:
receiving, by a system of one or more computers, an image of at least a portion of a whole specimen slide comprising a plurality of biological cells;
detecting, by the system, at least a portion of each of one or more individual cells within the plurality of cells;
determining, by the system, spatial coordinates for each of the one or more individual cells;
extracting, by the system, for each of the one or more individual cells, an extracted image of the individual cell, wherein the cell is centered on the extracted image, each extracted image representing an independent individual cell;
processing, by the system, the one or more extracted images to generate a cell type score for each extracted image;
extracting, by the system, a set of one or more of the extracted images having a cell type score within a predetermined range;
processing, by the system, each of the one or more extracted images within the set to generate an array of feature scores, wherein the array of feature scores comprises, for each image, a score for each of a plurality of features in a feature vector generated from the extracted image;
determining, by the system, a first set of metrics from the array of feature scores to generate an aggregated vector of integer or floating point numbers representing the at least a portion of the whole specimen slide; and
processing, by the system, the aggregated vector in a classifier to generate an output indicative of the presence or absence of a disease or disease type for the whole specimen slide or at least a portion of the whole specimen slide.

Embodiment 2

The method of embodiment 1, further comprising, prior to processing the set of extracted images, removing, by the system, background noise in each extracted image in the set.

Embodiment 3

The method of embodiment 2, wherein removing the background noise comprises generating a new image for each extracted image in the set using a watershed algorithm.

Embodiment 4

The method of embodiment 2, wherein removing the background noise comprises identifying the individual cell at the center of the extracted image and replacing all pixels outside the individual cell with a single color.

Embodiment 5

The method of any one of embodiments 1-4, further comprising ranking, by the system, each cell represented in the array of feature scores based on the array of feature scores.

Embodiment 6

The method of embodiment 5, wherein ranking each cell represented in the array of feature scores based on the array of feature scores comprises ranking based on one or more feature scores within the array of feature scores.

Embodiment 7

The method of any one of embodiments 5-6, further comprising selecting, by the system, a subset of cells represented in the array of feature scores based on a predetermined ranking range.

Embodiment 8

The method of embodiment 7, further comprising generating, by the system, an image gallery of the subset of cells.

Embodiment 9

The method of embodiment 8, further comprising outputting, by the system, a visual interface comprising the image gallery of the subset of cells.

Embodiment 10

The method of any one of embodiments 1-9, further comprising classifying, by the system, each cell represented in the array of feature scores into one of a plurality of predetermined cell-type clusters based on the array of feature scores.

Embodiment 11

The method of embodiment 10, wherein classifying comprises using a gaussian mixture model.

Embodiment 12

The method of any one of embodiments 10-11, further comprising determining, by the system, a proportion of cells in each predetermined cell-type cluster.

Embodiment 13

The method of embodiment 12, further comprising determining, by the system, a distance from each cell-type cluster center to each cell represented in the array of feature scores.

Embodiment 14

The method of embodiment 13, further comprising inputting, by the system, the distance and proportion data into the aggregated vector.

Embodiment 15

The method of any one of embodiments 1-14, further comprising, identifying, by the system, based on the spatial coordinates of each cell, potential cell clusters.

Embodiment 16

The method of embodiment 15, wherein identifying potential cell clusters comprises using a data clustering algorithm.

Embodiment 17

The method of embodiment 15, wherein identifying potential cell clusters comprises using a density-based spatial clustering of applications with noise algorithm.

Embodiment 18

The method of any one of embodiments 15-17, further comprising generating, by the system, an image of each potential cell cluster wherein each individual cluster is centered within its respective image.

Embodiment 19

The method of embodiment 18, wherein the image of each potential cell cluster is from about 400 to 600 pixels by about 400 to 600 pixels.

Embodiment 20

The method of embodiment 18, wherein the image of each potential cell cluster is from about 0.000015% to about 0.006% of the at least a portion of the whole slide image.

Embodiment 21

The method of any one of embodiments 15-20, further comprising determining, by the system, whether each potential cell cluster is a true cell cluster, where a true cell cluster is defined as a group of cells in spatial proximity when measured by the system and that naturally originated in spatial proximity.

Embodiment 22

The method of embodiment 21, wherein determining whether each potential cell cluster is a true cell cluster comprises processing, by the system, each image of each potential cell cluster.

Embodiment 23

The method of embodiment 22, wherein processing each image of each potential cell cluster comprises analyzing each image using a machine learning model.

Embodiment 24

The method of embodiment 23, wherein the machine learning model is deep learning.

Embodiment 25

The method of embodiment 15-24, further comprising determining, by the system, a second set of metrics for each potential cell cluster.

Embodiment 26

The method of embodiment 25, further comprising adding, by the system, the second set of metrics for each potential cell cluster to the aggregated vector.

Embodiment 27

The method of any one of embodiments 1-26, wherein extracting an image of an individual cell comprises identifying the pixels that comprise the cell or the nucleus of the cell, determining the minimum and maximum height and width limits of those pixels, and outputting a new image that is a subset of the original image including only the pixels within those limits.

Embodiment 28

The method of any one of embodiments 1-26, wherein extracting an image of an individual cell comprises identifying the center of the pixels that comprise the cell or the nucleus of the cell, determining the coordinates of the box that is formed by subtracting or adding a fixed number of pixels to the cell center coordinates, and outputting a new image that is a subset of the original image that includes only the pixels within those coordinates.

Embodiment 29

The method of any one of embodiments 1-28, wherein the cell type score represents an estimate of the likelihood that the cell is a target cell type.

Embodiment 30

The method of embodiment 29, wherein the target cell type is selected from the group consisting of urothelial cells, squamous epithelial cells, basal cells, follicular cells, glomerular cells, glandular cells, lymphocytes, monocytes, neutrophils, eosinophils, and combinations thereof.

Embodiment 31

The method of any one of embodiments 1-30, wherein the plurality of features are selected from the group consisting of cell-level features, slide-level features, and combinations thereof.

Embodiment 32

The method of any one of embodiments 1-30, wherein the plurality of features comprise one or more cell-level features selected from a plurality of cytomorphologic criteria.

Embodiment 33

The method of embodiment 32, wherein the cytomorphologic criteria are or are representative of cytomorphologic criteria used in diagnostic pathology methods.

Embodiment 34

The method of any one of embodiments 32-33, wherein the cytomorphologic criteria are or are representative of cytomorphologic criteria for reporting urinary cytology.

Embodiment 35

The method of any one of embodiments 31-34, wherein the one or more cell-level features are selected from the group consisting of nuclear-to-cytoplasmic ratio, nuclear hyperchromasia, chromatin coarseness, nuclear membrane irregularity, cellular degradation, malignancy value, focal score, nuclear-to-cytoplasmic pixel ratio, cell-in-cell arrangements, and combinations thereof.

Embodiment 36

The method of any one of embodiments 1-35, wherein the plurality of features comprise one or more slide-level features selected from the group consisting of target cell type count, target cell type proportion, total cells in slide, atypical cell count, atypical cell proportion, malignant cell count, degraded cell proportion, cell-in-cell arrangement count, and a cell cluster analysis parameter.

Embodiment 37

The method of embodiment 36, wherein the target cell type is urothelial cells.

Embodiment 38

The method of any one of embodiments 1-37, further comprising: receiving, by the system, data from one or more separate diagnostic tests; and
inputting, by the system, the data from the one or more separate diagnostic tests into the aggregated vector.

Embodiment 39

The method of embodiment 38, wherein the one or more separate diagnostic tests are selected from the group consisting of subject imaging, subject sample imaging, a blood test, a urine test, a fine needle aspirate test, a sputum test, a lumbar puncture test, and a pap smear test.

Embodiment 40

The method of any one of embodiments 38-39, wherein the one or more separate diagnostic tests comprise fluorescent in situ hybridization.

Embodiment 41

The method of any one of embodiments 1-40, wherein the disease or disease type is selected from the group consisting of high grade urothelial carcinoma, suspicious for high grade urothelial carcinoma, low grade urothelial neoplasia, atypical urothelial cells, and negative for high grade urothelial carcinoma.

Embodiment 42

The method of any one of embodiments 1-41, further comprising preparing the whole specimen slide from a biological sample.

Embodiment 43

The method of embodiment 42, wherein the biological sample is obtained from a subject.

Embodiment 44

The method of embodiment 43, wherein the subject is human.

Embodiment 45

The method of any one of embodiments 41-44, further comprising imaging the whole specimen slide to generate the image of the at least a portion of the whole specimen slide.

Embodiment 46

The method of embodiment 45, wherein the imaging comprises scanning the slide in a digital slide scanner.

Embodiment 47

The method of any one of embodiments 1-46 wherein each feature score is determined by an independent machine learning model.

Embodiment 48

The method of any one of embodiments 1-47, wherein the extracted image has a size of from about 100 to 200 pixels by about 100 to 200 pixels.

Embodiment 49

The method of any one of embodiments 1-48, wherein the at least a portion of the whole slide image has a size of from about 80,000 pixels to about 1,000,000 pixels by about 80,000 pixels to about 1,000,000 pixels.

Embodiment 50

The method of any one of embodiments 1-50, wherein the extracted image has a size of from about 0.0001% to about 0.005% of the size of the at least a portion of the whole slide image.

Embodiment 51

The method of any one of embodiments 1-50, wherein the first set of metrics comprise summary statistics.

Embodiment 52

The method of any one of embodiments 25-26, wherein the second set of metrics comprise summary statistics.

Embodiment 53

The method of any one of embodiments 51-52, wherein the summary statistics are selected from the group consisting of mean, median, standard deviation, variance, kurtosis, or skew, histograms, principal components analysis, and combinations thereof.

Embodiment 54

One or more non-transitory computer-readable media encoded with instructions that, when executed by one or more processors of a system, cause the one or more processors to perform operations comprising the method of any one of embodiments 1-53.

Embodiment 55

A computing system, comprising:
one or more processors; and
one or more computer-readable media encoded with instructions that, when executed by the one or more processors, cause the one or more processors to perform the method of any one of embodiments 1-53.

Embodiment 56

A system comprising:
a digital slide scanner; and
a computing system according to embodiment 55.

Embodiment 57

A method comprising:
accessing, at one or more computing devices, an image of at least a portion of a whole specimen slide comprising one or more biological cells;
determining, by the one or more computing devices, a presence or absence of a disease or disease type based on independent analysis by the one or more computing devices of each of two or more features of the at least a portion of the whole specimen slide image; and
providing, by the one or more computing devices, an output indicative of the presence or absence of a disease or disease type.

Embodiment 58

The method of embodiment 57, wherein the independent analysis comprises:
determining, by the one or more computing devices, based on a feature vector comprising a plurality of features that are extracted from the accessed image, a score for each of the features.

Embodiment 59

The method of embodiment 58, wherein the plurality of features comprises at least one cytomorphologic criteria.

Embodiment 60

The method of embodiment 59, wherein the cytomorphologic criteria is a cytomorphologic criteria for the analysis of a disease, organism, or cell.

Embodiment 61

The method of any one of embodiments 59-60, wherein the cytomorphologic criteria is a cytomorphologic criteria for the analysis of a cancer in an organism.

Embodiment 62

The method of embodiment 61, wherein the cancer is selected from thyroid cancer, lung cancer, brain cancer, kidney cancer, pancreatic cancer, breast cancer, biliary cancer, cervical cancer, or liver cancer.

Embodiment 63

The method of embodiment 62, wherein the cancer is bladder cancer.

Embodiment 64

The method of embodiment 63, wherein the bladder cancer is high grade urothelial carcinoma.

Embodiment 65

The method of any one of embodiments 57-64, wherein determining the presence or absence of a disease or disease type comprises using an image classification model stored in one or more memories of the one or more computing devices, the image classification being trained using supervised learning to extract a plurality of features from the image and independently classify images into a plurality of classes within each feature and being notified, via a graphical user interface (GUI), of a corresponding pathologist score for each class of each feature, the GUI displaying at least one image from each class of the plurality of classes within each feature, wherein the combined score of the plurality of features for each image corresponds to an indication of the presence or absence of a disease or disease type.

Embodiment 66

The method of any one of embodiments 57-65, wherein the output comprises at least one image of a single cell identified in the specimen slide image and a corresponding cell score computed by the one or more computing devices based on two or more independent feature scores determined by the one or more computing devices for each of two or more independent features of the specimen slide image.

Embodiment 67

The method of any one of embodiments 57-66, wherein the features are selected from cell-level features, slide-level features, and combinations thereof.

Embodiment 68

The method of any one of embodiments 57-67, wherein the features comprise one or more cell-level features selected from a plurality of cytomorphologic criteria.

Embodiment 69

The method of embodiment 68, wherein the cytomorphologic criteria are or are representative of cytomorphologic criteria used in diagnostic pathology methods.

Embodiment 70

The method of embodiment 68, wherein the cytomorphologic criteria are or are representative of cytomorphologic criteria for reporting urinary cytology.

Embodiment 71

The method of any one of embodiments 68-70, wherein the one or more cell-level features are selected from the group consisting of a nuclear-to-cytoplasmic ratio, nuclear hyperchromasia, chromatin coarseness, nuclear membrane irregularity, cellular degradation, malignancy classifier, malignancy value, focal score, nuclear-to-cytoplasmic pixel ratio, cell-in-cell arrangements, and combinations thereof.

Embodiment 72

The method of any one of embodiments 57-71, wherein the plurality of features comprise one or more slide-level features selected from the group consisting of target cell type count, target cell type proportion, total cells in slide, atypical cell count, atypical cell proportion, malignant cell count, degraded cell proportion, cell-in-cell arrangement count, and a cell cluster analysis parameter.

Embodiment 73

The method of embodiment 72, wherein the target cell type is urothelial cells.

Embodiment 74

The method of any one of embodiments 57-73, wherein the whole specimen slide is prepared from a biological sample.

Embodiment 75

The method of embodiment 74, wherein the biological sample is obtained from a subject.

Embodiment 76

The method of embodiment 75, wherein the subject is human.

Embodiment 77

The method of any one of embodiments 75-76, wherein determining the presence or absence of a disease or disease type is further based on one or more separate diagnostic tests performed on the subject.

Embodiment 78

The method of embodiment 77, wherein the one or more separate diagnostic tests are selected from the group consisting of subject imaging, subject sample imaging, a blood test, a urine test, a fine needle aspirate test, a sputum test, a lumbar puncture test, or a pap smear test.

Embodiment 79

The method of any one of embodiments 77-78, wherein the one or more separate diagnostic tests comprise fluorescent in situ hybridization.

Embodiment 80

The method of any one of embodiments 57-79, wherein the disease or disease type is selected from the group consisting of high grade urothelial carcinoma, suspicious for high grade urothelial carcinoma, low grade urothelial neoplasia, atypical urothelial cells, and negative for high grade urothelial carcinoma.

Embodiment 81

The method of any one of embodiments 57-80, wherein each feature is extracted and analyzed, by the one or more computing devices, using an independent machine learning model.

Embodiment 82

The method of embodiment 81, wherein each independent machine learning model is a deep learning model.

Embodiment 83

The method of any one of embodiments 57-82, wherein the presence or absence of a disease or disease type is determined based on a combined analysis comprising analysis of a nuclear-to-cytoplasmic ratio, nuclear hyperchromasia, chromatin coarseness, nuclear membrane irregularity, cellular degradation, a malignancy classifier, a malignancy value, a focal score, and a nuclear-to-cytoplasmic pixel ratio.

Embodiment 84

The method of embodiment 83, wherein the combined analysis further comprises urothelial cell count, urothelial cell proportion, total cells in slide, atypical cell count, atypical cell proportion, malignant cell count, and degraded cell proportion.

Embodiment 85

The method of embodiment 84, wherein the combined analysis further comprises cell cluster analysis.

Embodiment 86

The method of embodiment 85, wherein the cell cluster analysis is selected from the group consisting of cell-type cluster analysis, true cell cluster analysis, and combinations thereof.

Embodiment 87

The method of any one of embodiments 57-86 and 215-216, wherein the output comprises a cell count.

Embodiment 88

The method of any one of embodiments 57-87 and 215-216, wherein the output comprises cell type distribution.

Embodiment 89

The method of any one of embodiments 57-88 and 215-216, wherein the output comprises one or more feature scores.

Embodiment 90

The method of embodiment 89, wherein the output further comprises one or more comparative feature scores for each of one or more other collected specimens having a common clinical diagnosis, disease or disease type, feature score, clinical interpretation, or a combination thereof.

Embodiment 91

One or more non-transitory computer-readable media encoded with instructions that, when executed by one or more processors of a system, cause the one or more processors to perform operations comprising the method any one of embodiments 57-90 and 215-216.

Embodiment 92

A computing system, comprising:
one or more processors; and
one or more computer-readable media encoded with instructions that, when executed by the one or more processors, cause the one or more processors to perform the method of any one of embodiments 57-90 and 215-216.

Embodiment 93

A system comprising:
a digital slide scanner; and
a computing system according to embodiment 92.

Embodiment 94

A method, comprising:
identifying, by a system of one or more computers, a feature vector that represents cytomorphologic criteria for each of one or more individual cells within a plurality of cells in at least a portion of a whole specimen slide image;
generating, by the system, for each of the one or more individual cells, an array of feature scores, wherein the array of feature scores comprises a score for each of a plurality of features in the feature vector;
processing, by the system, the array of feature scores to identify one or more diagnostic cells within the plurality of cells, wherein the one or more diagnostic cells are useful for determining the presence or absence of a disease or disease type; and
providing, by the system, one or more outputs indicative of the one or more diagnostic cells.

Embodiment 95

The method of embodiment 94, further comprising, prior to identifying the feature vector:
receiving, by the system, an image of at least a portion of a whole specimen slide comprising a plurality of biological cells;
detecting, by the system, at least a portion of each of one or more individual cells within the plurality of cells; and
determining, by the system, spatial coordinates for each of the one or more individual cells.

Embodiment 96

The method of embodiment 95, further comprising extracting, by the system, for each of the one or more individual cells, an extracted image of the individual cell, wherein the cell is centered on the extracted image, each extracted image representing an independent individual cell.

Embodiment 97

The method of embodiment 96, wherein extracting an image of an individual cell comprises identifying the pixels that comprise the cell or the nucleus of the cell, determining the minimum and maximum height and width limits of those pixels, and outputting a new image that is a subset of the original image including only the pixels within those limits.

Embodiment 98

The method of embodiment 96, wherein extracting an image of an individual cell comprises identifying the center of the pixels that comprise the cell or the nucleus of the cell, determining the coordinates of the box that is formed by subtracting and adding a fixed number of pixels to the cell center coordinates, and outputting a new image that is a subset of the original image that includes only the pixels within those coordinates.

Embodiment 99

The method of any one of embodiments 96-98, wherein the extracted image has a size of from about 100 to 200 pixels by about 100 to 200 pixels.

Embodiment 100

The method of any one of embodiments 96-98, wherein the at least a portion of the whole slide image has a size of from about 80,000 pixels to about 1,000,000 pixels by about 80,000 pixels to about 1,000,000 pixels.

Embodiment 101

The method of any one of embodiments 96-98, wherein the extracted image has a size of from about 0.0001% to about 0.005% of the size of the at least a portion of the whole slide image.

Embodiment 102

The method of any one of embodiments 96-101, further comprising:
processing, by the system, the one or more extracted images to generate a cell type score for each extracted image; and

Embodiment 103

The method of embodiment 102, wherein the cell type score represents an estimate of the likelihood that the cell is a target cell type.

Embodiment 104

The method of embodiment 103, wherein the target cell type is selected from the group consisting of urothelial cells, squamous epithelial cells, basal cells, follicular cells, glomerular cells, glandular cells, lymphocytes, monocytes, neutrophils, eosinophils, and combinations thereof.

Embodiment 105

The method of any one of embodiments 94-104, further comprising ranking, by the system, each cell represented in the array of feature scores based on the array of feature scores.

Embodiment 106

The method of embodiment 105, wherein ranking each cell represented in the array of feature scores based on the array of feature scores comprises ranking based on one or more feature scores within the array of feature scores.

Embodiment 107

The method of any one of embodiments 105-106, further comprising selecting, by the system, a subset of cells represented in the array of feature scores based on a predetermined ranking range.

Embodiment 108

The method of embodiment 107, further comprising generating, by the system, an image gallery of the subset of cells.

Embodiment 109

The method of embodiment 108, further comprising outputting, by the system, a visual interface comprising the image gallery of the subset of cells.

Embodiment 110

The method of any one of embodiments 94-109, further comprising classifying, by the system, each cell represented in the array of feature scores into one of a plurality of predetermined cell-type clusters based on the array of feature scores.

Embodiment 111

The method of embodiment 110, wherein classifying comprises using a gaussian mixture model.

extracting, by the system, a set of one or more of the extracted images having a cell type score within a predetermined range.

Embodiment 112

The method of any one of embodiments 110-111, further comprising determining, by the system, a proportion of cells in each predetermined cell-type cluster.

Embodiment 113

The method of embodiment 112, further comprising determining, by the system, a distance from each cell-type cluster center to each cell represented in the array of feature scores.

Embodiment 114

The method of any one of embodiments 94-113, wherein each feature score is determined by an independent machine learning model.

Embodiment 115

The method of any one of embodiments 94-114, wherein the plurality of features comprise one or more cell-level features selected from a plurality of cytomorphologic criteria.

Embodiment 116

The method of embodiment 115, wherein the cytomorphologic criteria are or are representative of cytomorphologic criteria used in diagnostic pathology methods.

Embodiment 117

The method of any one of embodiments 115-116, wherein the cytomorphologic criteria are or are representative of cytomorphologic criteria for reporting urinary cytology.

Embodiment 118

The method of any one of embodiments 115-117, wherein the one or more cell-level features are selected from the group consisting of a nuclear-to-cytoplasmic ratio, nuclear hyperchromasia, chromatin coarseness, nuclear membrane irregularity, cellular degradation, malignancy classifier, malignancy value, focal score, nuclear-to-cytoplasmic pixel ratio, cell-in-cell arrangements, and combinations thereof.

Embodiment 119

The method of any one of embodiments 94-118, wherein processing the array of feature scores further comprises:
determining, by the system, a first set of metrics from the array of feature scores;
generating, by the system, based on the first set of metrics, an aggregated vector of integer or floating point numbers representing the at least a portion of the whole specimen slide; and processing, by the system, the aggregated vector in a machine learning model.

Embodiment 120

The method of embodiment 119, wherein the first set of metrics comprise summary statistics.

Embodiment 121

The method of embodiment 120, wherein the summary statistics are selected from the group consisting of mean, median, standard deviation, variance, kurtosis, or skew, histograms, principal components analysis, and combinations thereof.

Embodiment 122

The method of any one of embodiments 94-121, further comprising preparing the whole specimen slide from a biological sample.

Embodiment 123

The method of embodiment 122, wherein the biological sample is obtained from a subject.

Embodiment 124

The method of embodiment 123, wherein the subject is human.

Embodiment 125

The method of any one of embodiments 122-124, further comprising imaging the whole specimen slide to generate the image of at least a portion of the whole specimen slide.

Embodiment 126

The method of embodiment 125, wherein the imaging comprises scanning the slide in a digital slide scanner.

Embodiment 127

The method of any one of embodiments 94-126, wherein the one or more outputs are selected from the group consisting of summary statistics, a cell type cluster score, one or more feature scores, an image of each of one or more diagnostic cells, a composite image having a plurality of images of multiple diagnostic cells, and combinations thereof.

Embodiment 128

The method of embodiment 102, further comprising, prior to processing the one or more extracted images, removing, by the system, background noise in each extracted image in the set.

Embodiment 129

The method of embodiment 128, wherein removing the background noise comprises generating a new image for each extracted image in the set using a watershed algorithm.

Embodiment 130

The method of embodiment 128, wherein removing the background noise comprises identifying the individual cell at the center of the extracted image and replacing all pixels outside the individual cell with a single color.

Embodiment 131

The method of any one of embodiments 94-130, further comprising determining, based on the one or more diagnostic cells, the presence or absence of a disease or disease type for the whole specimen slide or the at least a portion of the whole specimen slide.

Embodiment 132

The method of embodiment 131, wherein the disease or disease type is selected from the group consisting of high grade urothelial carcinoma, suspicious for high grade urothelial carcinoma, low grade urothelial neoplasia, atypical urothelial cells, and negative for high grade urothelial carcinoma.

Embodiment 133

A method, comprising:
accessing, at one or more computing devices, an image of at least a portion of a whole specimen slide comprising a plurality of biological cells;
identifying, by the one or more computing devices, a feature vector that represents cytomorphologic criteria for each of one or more individual cells within the plurality of cells;
processing, by the one or more computing devices, two or more features of the feature vector to identify one or more diagnostic cells within the plurality of cells, wherein the one or more diagnostic cells are useful for determining the presence or absence of a disease or disease type; and providing, by the one or more computing devices, one or more outputs indicative of the one or more diagnostic cells.

Embodiment 134

A method, comprising:
identifying, by a system of one or more computers, a feature vector that represents cytomorphologic criteria for each of one or more individual cells within a plurality of cells in at least a portion of a whole specimen slide image;
generating, by the system, for each of the one or more individual cells, an array of feature scores, wherein the array of feature scores comprises a score for each of a plurality of features in the feature vector;
determining, by the system, a presence or absence of a disease or disease type for the at least a portion of the whole specimen slide based on the array of feature scores; and
providing, by the system, an output indicative of the presence or absence of a disease or disease type for the whole specimen slide or the at least a portion of the whole specimen slide.

Embodiment 135

The method of embodiment 134, further comprising, prior to identifying the feature vector:
receiving, by the system, an image of at least a portion of a whole specimen slide comprising a plurality of biological cells;
detecting, by the system, at least a portion of each of one or more individual cells within the plurality of cells; and
determining, by the system, spatial coordinates for each of the one or more individual cells.

Embodiment 136

The method of embodiment 135, further comprising extracting, by the system, for each of the one or more individual cells, an extracted image of the individual cell, wherein the cell is centered on the extracted image, each extracted image representing an independent individual cell.

Embodiment 137

The method of embodiment 136, wherein extracting an image of an individual cell comprises identifying the pixels that comprise the cell or the nucleus of the cell, determining the minimum and maximum height and width limits of those pixels, and outputting a new image that is a subset of the original image including only the pixels within those limits.

Embodiment 138

The method of embodiment 136, wherein extracting an image of an individual cell comprises identifying the center of the pixels that comprise the cell or the nucleus of the cell, determining the coordinates of the box that is formed by subtracting and adding a fixed number of pixels to the cell center coordinates, and outputting a new image that is a subset of the original image that includes only the pixels within those coordinates.

Embodiment 139

The method of any one of embodiments 136-138, wherein the extracted image has a size of from about 100 to 200 pixels by about 100 to 200 pixels.

Embodiment 140

The method of any one of embodiments 136-138, wherein the at least a portion of the whole slide image has a size of from about 80,000 pixels to about 1,000,000 pixels by about 80,000 pixels to about 1,000,000 pixels.

Embodiment 141

The method of any one of embodiments 136-138, wherein the extracted image has a size of from about 0.0001% to about 0.005% of the size of the at least a portion of the whole slide image.

Embodiment 142

The method of any one of embodiments 136-141, further comprising:
processing, by the system, the one or more extracted images to generate a cell type score for each extracted image; and
extracting, by the system, a set of one or more of the extracted images having a cell type score within a predetermined range.

Embodiment 143

The method of embodiment 142, wherein the cell type score represents an estimate of the likelihood that the cell is a target cell type.

Embodiment 144

The method of embodiment 143, wherein the target cell type is selected from the group consisting of urothelial cells, squamous epithelial cells, basal cells, follicular cells, glomerular cells, glandular cells, lymphocytes, monocytes, neutrophils, eosinophils, and combinations thereof.

Embodiment 145

The method of any one of embodiments 134-144, further comprising ranking, by the system, each cell represented in the array of feature scores based on the array of feature scores.

Embodiment 146

The method of embodiment 145, wherein ranking each cell represented in the array of feature scores based on the array of feature scores comprises ranking based on one or more feature scores within the array of feature scores.

Embodiment 147

The method of any one of embodiments 145-146, further comprising selecting, by the system, a subset of cells represented in the array of feature scores based on a predetermined ranking range.

Embodiment 148

The method of embodiment 147, further comprising generating, by the system, an image gallery of the subset of cells.

Embodiment 149

The method of embodiment 148, further comprising outputting, by the system, a visual interface comprising the image gallery of the subset of cells.

Embodiment 150

The method of any one of embodiments 134-149, further comprising classifying, by the system, each cell represented in the array of feature scores into one of a plurality of predetermined cell-type clusters based on the array of feature scores.

Embodiment 151

The method of embodiment 150, wherein classifying comprises using a gaussian mixture model.

Embodiment 152

The method of any one of embodiments 150-151, further comprising determining, by the system, a proportion of cells in each predetermined cell-type cluster.

Embodiment 153

The method of embodiment 152, further comprising determining, by the system, a distance from each cell-type cluster center to each cell represented in the array of feature scores.

Embodiment 154

The method of any one of embodiments 134-153, wherein each feature score is determined by an independent machine learning model.

Embodiment 155

The method of any one of embodiments 134-154, wherein the plurality of features comprise one or more cell-level features selected from a plurality of cytomorphologic criteria.

Embodiment 156

The method of embodiment 155, wherein the cytomorphologic criteria are or are representative of cytomorphologic criteria used in diagnostic pathology methods.

Embodiment 157

The method of any one of embodiments 155-156, wherein the cytomorphologic criteria are or are representative of cytomorphologic criteria for reporting urinary cytology.

Embodiment 158

The method of any one of embodiments 155-157, wherein the one or more cell-level features are selected from the group consisting of a nuclear-to-cytoplasmic ratio, nuclear hyperchromasia, chromatin coarseness, nuclear membrane irregularity, cellular degradation, malignancy classifier, malignancy value, focal score, nuclear-to-cytoplasmic pixel ratio, cell-in-cell arrangements, and combinations thereof.

Embodiment 159

The method of any one of embodiments 134-158, wherein processing the array of feature scores further comprises:
determining, by the system, a first set of metrics from the array of feature scores;
generating, based on the first set of metrics, an aggregated vector of integer or floating point numbers representing the at least a portion of the whole specimen slide; and
processing the aggregated vector.

Embodiment 160

The method of embodiment 159, wherein the first set of metrics comprise summary statistics.

Embodiment 161

The method of embodiment 160, wherein the summary statistics are selected from the group consisting of mean, median, standard deviation, variance, kurtosis, or skew, histograms, principal components analysis, and combinations thereof.

Embodiment 162

The method of any one of embodiments 134-161, further comprising preparing the whole specimen slide from a biological sample.

Embodiment 163

The method of embodiment 162, wherein the biological sample is obtained from a subject.

Embodiment 164

The method of embodiment 163, wherein the subject is human.

Embodiment 165

The method of any one of embodiments 162-164, further comprising imaging the whole specimen slide to generate the image of the at least a portion of the whole specimen slide.

Embodiment 166

The method of embodiment 165, wherein the imaging comprises scanning the slide in a digital slide scanner.

Embodiment 167

The method of any one of embodiments 134-166, wherein the one or more outputs are selected from the group consisting of summary statistics, a cell type cluster score, one or more feature scores, an image of each of one or more diagnostic cells, a composite image having a plurality of images of multiple diagnostic cells, and combinations thereof.

Embodiment 168

The method of embodiment 142, further comprising, prior to processing the one or more extracted images, removing, by the system, background noise in each extracted image in the set.

Embodiment 169

The method of embodiment 168, wherein removing the background noise comprises generating a new image for each extracted image in the set using a watershed algorithm.

Embodiment 170

The method of embodiment 168, wherein removing the background noise comprises identifying the individual cell at the center of the extracted image and replacing all pixels outside the individual cell with a single color.

Embodiment 171

The method of any one of embodiments 134-170, wherein the disease or disease type is selected from the group consisting of high grade urothelial carcinoma, suspicious for high grade urothelial carcinoma, low grade urothelial neoplasia, atypical urothelial cells, and negative for high grade urothelial carcinoma.

Embodiment 172

The method of embodiments 135, further comprising, identifying, by the system, based on the spatial coordinates of each cell, potential cell clusters.

Embodiment 173

The method of embodiment 172, wherein identifying potential cell clusters comprises using a data clustering algorithm.

Embodiment 174

The method of embodiment 172, wherein identifying potential cell clusters comprises using a density-based spatial clustering of applications with noise algorithm.

Embodiment 175

The method of any one of embodiments 172-174, further comprising generating, by the system, an image of each potential cell cluster wherein each individual cluster is centered within its respective image.

Embodiment 176

The method of embodiment 175, wherein the image of each potential cell cluster is from about 400 to 600 pixels by about 400 to 600 pixels.

Embodiment 177

The method of embodiment 176, wherein the image of each potential cell cluster is from about 0.000015% to about 0.006% of the at least a portion of the whole slide image.

Embodiment 178

The method of any one of embodiments 172-177, further comprising determining, by the system, whether each potential cell cluster is a true cell cluster, where a true cell cluster is defined as a group of cells in spatial proximity when measured by the system and that naturally originated in spatial proximity.

Embodiment 179

The method of embodiment 178, wherein determining whether each potential cell cluster is a true cell cluster comprises processing, by the system, each image of each potential cell cluster.

Embodiment 180

The method of embodiment 179, wherein processing each image of each potential cell cluster comprises analyzed each image using a machine learning model.

Embodiment 181

The method of embodiment 180, wherein the machine learning model is deep learning.

Embodiment 182

The method of embodiment 172-179, further comprising determining, by the system, a second set of metrics for each potential cell cluster.

Embodiment 183

A method, comprising:
accessing, at one or more computing devices, an image of at least a portion of a whole specimen slide comprising a plurality of biological cells;
identifying, by the one or more computing devices, a feature vector that represents cytomorphologic criteria for each of one or more individual cells within the plurality of cells;
determining, by the one or more computing devices, a presence or absence of a disease or disease type for the at least a portion of the whole specimen slide based on independent analysis by the one or more computing devices of each of two or more features of the feature vector; and providing, by the one or more computing devices, an output indicative of the presence or absence of a disease or disease type.

Embodiment 184

A method, comprising:
accessing, at one or more computing devices, an image of at least a portion of a whole specimen slide comprising a plurality of biological cells;
detecting, by a system of one or more computing devices, at least a portion of each of one or more individual cells within the plurality of cells;
determining, by the system, spatial coordinates for each of the one or more individual cells;
extracting, by the system, for each of the one or more individual cells, an extracted image of the individual cell, wherein the cell is centered on the extracted image, each extracted image representing an independent individual cell;
processing, by the system, the one or more extracted images in a cell diagnosis machine learning system; and
providing, by the system, one or more outputs selected from the group consisting of an output indicative of the presence or absence of a disease or disease type for the at least a portion of the whole specimen slide, an output indicative of the presence or absence of a disease or disease type for each individual cell, an output indicative of one or more diagnostic cells useful for determining the presence or absence of a disease or disease type, and combinations thereof.

Embodiment 185

A method, comprising:
accessing, at one or more computing devices, an image of at least a portion of a whole specimen slide comprising a plurality of biological cells;
detecting, by a system of one or more computing devices, at least a portion of each of one or more individual cells within the plurality of cells;
determining, by the system, spatial coordinates for each of the one or more individual cells;
identifying, by the system, based on the spatial coordinates of each cell, one or more potential cell clusters; and
providing, by the system, an output indicative of the one or more potential cell clusters.

Embodiment 186

The method of embodiment 185, wherein identifying potential cell clusters comprises using a data clustering algorithm.

Embodiment 187

The method of embodiment 185, wherein identifying potential cell clusters comprises using a density-based spatial clustering of applications with noise algorithm.

Embodiment 188

The method of any one of embodiments 185-187, further comprising generating, by the system, an image of each potential cell cluster wherein each individual cluster is centered within its respective image.

Embodiment 189

The method of embodiment 188, wherein the image of each potential cell cluster is from about 400 to 600 pixels by about 400 to 600 pixels.

Embodiment 190

The method of embodiment 188, wherein the image of each potential cell cluster is from about 0.000015% to about 0.006% of the at least a portion of the whole slide image.

Embodiment 191

The method of any one of embodiments 185-190, further comprising determining, by the system, whether each potential cell cluster is a true cell cluster, where a true cell cluster is defined as a group of cells in spatial proximity when measured by the system and that naturally originated in spatial proximity.

Embodiment 192

The method of embodiment 191, wherein determining whether each potential cell cluster is a true cell cluster comprises processing, by the system, each image of each potential cell cluster.

Embodiment 193

The method of embodiment 192, wherein processing each image of each potential cell cluster comprises analyzed each image using a machine learning model.

Embodiment 194

The method of embodiment 193, wherein the machine learning model is deep learning.

Embodiment 195

One or more non-transitory computer-readable media encoded with instructions that, when executed by one or more processors of a system, cause the one or more processors to perform operations comprising the method any one of embodiments 94-194.

Embodiment 196

A computing system, comprising:
one or more processors; and
one or more computer-readable media encoded with instructions that, when executed by the one or more processors, cause the one or more processors to perform the method of any one of embodiments 94-194.

Embodiment 197

A system comprising:
a digital slide scanner; and
a computing system according to embodiment 196.

Embodiment 198

A method of diagnosing, in a subject, a condition selected from the group consisting of high grade urothelial carcinoma, suspicious for high grade urothelial carcinoma, low grade urothelial neoplasia, atypical urothelial cells, and negative for high grade urothelial carcinoma comprising:
determining the presence or absence of a disease or disease type according to the method of any one of embodiments 1-53, 57-90, and 94-194.

Embodiment 199

A method of evaluating the effectiveness of a cancer intervention measure in a subject having or at risk for developing a cancer, comprising:
determining the existence of cancerous or precancerous cells according to the method of any one of embodiments 1-53, 57-90, and 94-194;
applying at least one intervention measure that is commensurate with the treatment or prevention of the cancer; and
determining the effectiveness of the intervention measure.

Embodiment 200

The method of embodiment 199, wherein the cancer is selected from the group consisting of thyroid cancer, lung cancer, brain cancer, kidney cancer, pancreatic cancer, breast cancer, biliary cancer, cervical cancer, or liver cancer.

Embodiment 201

The method of any one of embodiments 199-200, wherein the intervention method is selected from the group consisting of surgery, chemotherapy, radiation therapy, immunotherapy, hormone therapy, stem cell transplantation, diet intervention, lifestyle intervention, and combinations thereof.

Embodiment 202

A visual interface comprising:
an image of at least a portion of a whole specimen slide including biological cells, overlaid with a visual representation of a prediction score for each of one or more cells identified in the slide.

Embodiment 203

The visual interface of embodiment 202, wherein the prediction score provides a visual indication of an importance score for each identified cell based on the cell's importance in determining the presence or absence of a disease or disease type.

Embodiment 204

The visual interface of embodiment 202, wherein the prediction score provides a visual indication of a point on a severity scale indicative of a severity of a disease or disease type.

Embodiment 205

The visual interface of embodiment 202, wherein the prediction score provides a visual indication of an overall predicted malignancy for the whole slide or at least a portion of the whole slide.

Embodiment 206

The visual interface of embodiment 202, wherein the prediction score provides a visual indication of a value of an individual cytomorphologic criteria feature score.

Embodiment 207

The visual interface of any one of embodiments 202-206, wherein the prediction score is a numerical value that specifies, or is used to compute at least one of a grayscale, a shading type, a color, and a second numerical value.

Embodiment 208

A visual interface comprising:
a collection of images, each image being of an individual cell and extracted from at least a portion of a whole specimen slide image comprising a plurality of cells; and
one or more scores corresponding to each of one or more cytomorphologic criteria features.

Embodiment 209

A visual interface comprising:
a single composite image comprising a plurality of selected individual cell images extracted from at least a portion of a whole specimen slide image comprising a plurality of cells.

Embodiment 210

The visual interface of embodiment 209, wherein the selected cells consist of cells identified as exceeding a predetermined threshold based on a presence or absence of a disease or disease type determined from a combination of individual cytomorphologic criteria feature scores.

Embodiment 211

A visual interface comprising: a collection of images, each image being of an individual true cell cluster and extracted from at least a portion of a whole specimen slide image comprising a plurality of cells and true cell clusters; and
one or more scores corresponding to a presence or absence of a cellular or whole slide disease or disease type.

Embodiment 212

A method of improving image-based cell identification, classification, or analysis of one or more individual cells in an image comprising:
extracting, for each of the one or more individual cells, an extracted image of the individual cell, wherein the cell is centered on the extracted image;
removing background noise in the extracted image.

Embodiment 213

The method of embodiment 212, wherein removing the background noise comprises generating a new image for each extracted image using a watershed algorithm.

Embodiment 214

The computer-implemented method of embodiment 212, wherein removing the background noise comprises identifying the cell at the center of the extracted image and replacing all pixels outside the cell with a single color.

Embodiment 215

The method of any one of embodiments 57-82, wherein the presence or absence of a disease or disease type is determined based on a combined analysis of the two or more features.

Embodiment 216

The method of embodiment 215, wherein the combined analysis comprises:
extracting and analyzing, by the one or more computing devices, each of the two or more features using an independent machine learning model to generate one or more feature scores for each of the features; and
processing, by the one or more computing devices, the feature scores together using a machine learning model.

Embodiment 217

A method of producing one or more single composite images comprising a plurality of selected individual cell images extracted from at least a portion of a whole specimen slide image having a plurality of cells, the method comprising:
generating, by a system of one or more computing devices, a plurality of composite images, each comprising a different amount of selected individual cell images extracted from at least a portion of the whole specimen slide;
training the system using supervised learning;
determining, by the system, a selected amount of individual cell images useful for whole slide diagnosis; and
producing, by the system, the one or more single composite images comprising the selected amount of individual cell images.

Embodiment 218

A method comprising
identifying, by a system of one or more computers, features representing cytomorphologic criteria for each of one or more individual cells in an image of at least a portion of a specimen slide;
generating, by the system, for each of the one or more individual cells, feature scores for corresponding features,
determining, by the system, a presence or absence of a disease or disease type for the whole specimen slide based on the feature scores; and
providing, by the system, an output indicative of the presence or absence of a disease or disease type for the whole specimen slide.

Embodiment 219

A method, comprising:
identifying, by a system of one or more computers, a feature vector that represents cytomorphologic criteria for each of one or more individual cells in at least a portion of a slide image;
generating, by the system, for each of the one or more individual cells, feature scores, for corresponding features in the feature vector;
determining, by the system, a presence or absence of a disease or disease type for the for the whole specimen from which the slide image is derived based on the feature scores; and
providing, by the system, an output indicative of the presence or absence of a disease or disease type for the whole specimen from which the slide image is derived.

Embodiment 220

The method of embodiment 219, comprising, prior to identifying the feature vector:
receiving, by the system, the slide image; and
detecting, by the system, at least a portion of each of the one or more individual cells.

Embodiment 221

The method of embodiment 220, comprising:
determining, by the system, spatial coordinates for each of the one or more individual cells.

Embodiment 222

The method of any one of embodiments 219-221, comprising extracting, by the system, for each of the one or more individual cells, an extracted image of the individual cell, each extracted image representing an independent individual cell.

Embodiment 223

The method of embodiment 222, wherein the each cell is centered on each extracted image.

Embodiment 224

The method of embodiment 223, comprising:
processing, by the system, the one or more extracted images to generate a cell type score for each of the extracted images; and
identifying, by the system, one or more of the extracted images having a cell type score within a predetermined range.

Embodiment 225

The method embodiment 224, wherein the cell type score represents an estimate of a likelihood that the cell comprises a target cell type.

Embodiment 226

The method of any one of embodiments 219-225, comprising ranking, by the system, each cell represented in the feature scores based on the feature scores.

Embodiment 227

The method of any one of embodiments 219-226, comprising classifying, by the system, using a Gaussian mixture model, each cell represented in the feature scores into a predetermined cell-type cluster based on the feature scores.

Embodiment 228

The method of any one of embodiments 219-227, comprising determining each feature score by an independent machine learning model.

Embodiment 229

The method of any one of embodiments 219-228, wherein the features comprise one or more cell-level features selected from cytomorphologic criteria.

Embodiment 230

The method of any one of embodiments 219-229, wherein processing the feature scores comprises:
determining, by the system, first metrics from the feature scores;
generating, by the system, based on the first metrics, an aggregation of integer or floating point numbers representing the whole specimen slide; and
processing, by the system, the aggregation in a machine learning model.

Embodiment 231

The method of any one of embodiments 219-230, wherein the first metrics comprise summary statistics selected from the group consisting of mean, median, standard deviation, variance, kurtosis, or skew, histograms, principal components analysis, and combinations thereof.

Embodiment 232

The method of any one of embodiments 219-231, wherein the one or more outputs are selected from the group consisting of summary statistics, a cell type cluster score, one or more feature scores, an image of each of one or more cells, a composite image having a plurality of images of multiple cells, and combinations thereof.

Embodiment 233

The method of any one of embodiments 222-223, further comprising, prior to processing the one or more extracted images, removing, by the system, background noise in each extracted image.

Embodiment 234

A visual interface comprising:
a single composite displayed image comprising selected individual cell images extracted from a whole specimen slide image comprising individual cells.

EXAMPLES

Example 1

Methods

Training slides were obtained from a mix of historical cases and recent clinical practice, enriched for suspicious and high grade specimens. Validation slides came from a date range of all clinical specimens processed at a local hospital for a 6-month date range. All slides were scanned on an Aperio AT2 slide scanner at the hospital. Scanned slides were de-identified and processed by in a HIPAA-compliant cloud environment using a system similar to that described in FIG. 6, according to the following process. A sample (e.g. urine) was acquired from the patient. The sample was spun down and filtered. A glass slide was prepared (e.g. using the ThinPrep system). The slide was scanned by a digital slide scanner. A whole slide image (e.g. 90,000 pixels by 90,000 pixels) was created. The whole slide image file was transferred to the HIPAA-compliant cloud-based system. Cell detection was performed on the entire whole slide image. A list of the <x,y> coordinates for all detected cells was generated. For each cell in the list, a small image (e.g. 150 pixels×150 pixels) was extracted, centered on the cell. Each image was processed by a deep learning-based cell type classifier that generates a score predicting how likely the image is to be the cell type of interest. As an optional step not necessarily used in this example, for each cell image that passed the cell type criteria (e.g. above a urothelial cell probability threshold), a watershed method could be performed to remove background noise, creating a new image. For each cell image that passed the cell type criteria, the image was processed by the deep learning-based clinical guidelines (e.g. PARIS) classifiers, optionally as well as degradation, malignancy, focal/blur score, and nucleus:cytoplasm pixel ratio. The scores for each of these calculations were saved to a large table with a row for each cell and a column for each score. As an optional step, a ranking algorithm could be used to select the most significant cells from the large table from which a cell image gallery was created. Summary statistics (e.g., mean, standard deviation, kurtosis, skew) were calculated from the large table of cellular scores to create a single aggregated vector of floating point numbers representing the whole slide. As an optional step, the table of cellular feature scores could be provided to a Gaussian mixture model. The model can calculate proportions of cells in one of three cell type clusters, as well as the average distance from each cluster center to the cell. These values could be added to the vector representing the whole slide. As an optional step, a separate cell cluster analysis module can be given the list of spatial cell <x,y> coordinates and use the coordinates to detect potential cell clusters (e.g. using DBSCAN). A medium-scale image (e.g. 500 pixels by 500 pixels) centered on the cell cluster could then be extracted. A deep learning model could then be applied to predict whether the cluster is a true cell cluster. Summary statistics could be calculated from these clusters and added to the vector representing the whole slide. Finally, the vector (see total possible vector details below) was provided as input to a whole slide classifier that predicts the clinical diagnosis (i.e. negative, atypical, low-grade, suspicious, high-grade) for the whole slide.

WSI Possible Vector Details (Including Optional Steps)
1. Cell-level Features
   A. PARIS Features—4 features, 2 model types (classifier, regressor). Each feature has 4 statistics calculated, and cell counts across 5 bins to better capture the distribution of the feature.

Sub-total=4*2*(4+5)=72 features

B. Pixel Ratio
      5 histograms and 4 statistics of NC pixel ratio for a cell.
      Sub-total=9 features
   C. Malignant Classifier
      4 statistics for malignant classifier and malignancy value.
      Sub-total=5 features
2. Slide-level Features
   A. Features summarizing slide, with respect to individual cells
      a. Urothelial cell count, urothelial cell proportion, Total cells in slide=3 features
      b. Atypical cell count, cell-in-cell arrangement count, atypical cell proportion, malignant cell count, degraded cell proportion*2 models+malignant cell counts from malignant classifier=9 features
      c. Proportion of urothelial cells in 3 GMM clusters, 4 statistics about the cell=5*3=15 features
      Sub-total=27 features
   B. Features summarizing cell clusters in the slide
      Average Urotheliarity of each cell in the cluster, # Urothelial cells per cluster=2 features.
      Avg of 4 PARIS features+degradation of cells in a cluster*2 models=10 features
      Number of urothelial clusters in the slide=1 feature
      Sub-total=13 features
Total=126 features Results ThinPrep slides from urine samples were obtained for training (n=1615) and validation (n=790). Table 1 describes relevant characteristics of the two data sets. The sample type (voided vs. catheterized) and scan adequacy proportions were similar between the two data sets. The proportion of high-grade or suspicious for high-grade cases was significantly lower in the validation dataset, as expected.

TABLE 1

Data set characteristics

| Characteristics | Development Data Set | Validation Data Sat |
|---|---|---|
| Number of slides | 1615 | 790 |
| Voided, No. (%) | 991 (69.0%) | 580 (73.4%) |
| Catheterized, No. (%) | 263 (18.3%) | 40 (5.1%) |
| Scan adequacy, No. (%) | 1436 (88.9%) | 744 (84.2%) |
| Low cellularity, No. (%) | 116 (7.2%) | 25 (3.2%) |
| Operator error, No. (%) | 26 (1.6%) | 11 (1.4%) |
| Blurry/degraded, No. (%) | 37 (2.3%) | 8 (1.0%) |
| High-grade/Suspicious, No. (%) | 490 (30.3%) | 44 (5.66%) |

Figure 9:
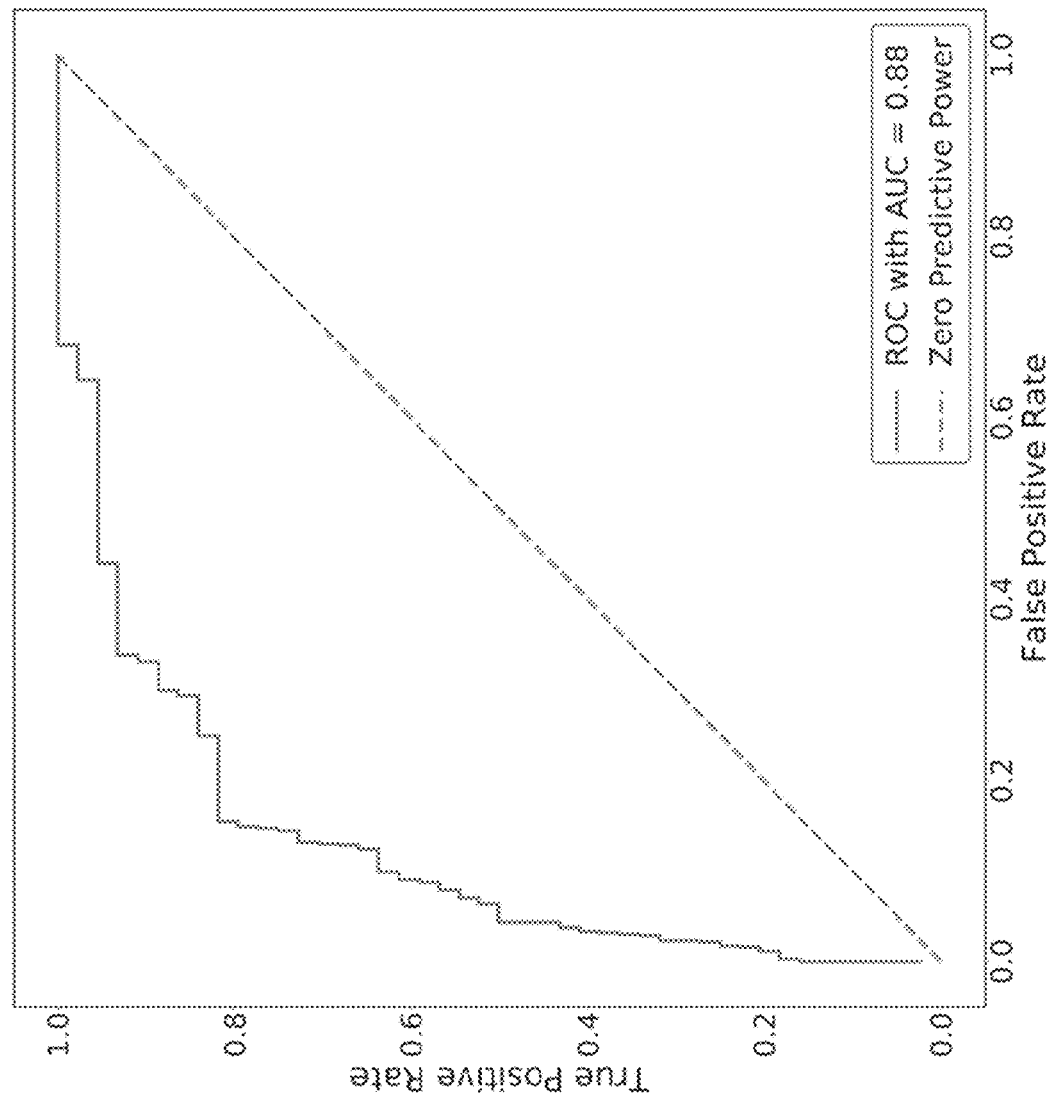
FIG. 9 is a validation dataset algorithm receiver operating characteristic curve graph showing concordance between an exemplary system and a pathologist for predicting a positive (SHGUC/HGUC) diagnosis according to Example 1.

FIG. 9 shows a receiver operating characteristic curve for major discordance with pathologist diagnosis, indicating the concordance of the algorithm with respect to the pathologist diagnosis under a two-class system (Negative/Atypical vs. Low-grade/Suspicious/High-grade), with an area under the curve (AUC) value of 0.88.

Based on the optimal operating point in FIG. 1, a 2×2 table was generated to characterize the sensitivity and specificity of the algorithm (Table 2). While a significant number of false positives were observed leading to a low positive predictive value (24.4%), the algorithm had strong values for negative predictive value (97.6%) and specificity (87.1%), while maintaining a reasonable sensitivity (65.9%). When evaluated against histology as ground truth, studies show urine cytology itself has similar sensitivity and specificity (60.9% and 83.8%, Dimashkieh H, Wolff D, Smith T, Houser P, Nietert P, Yang J. Evaluation of UroVysion and Cytology for Bladder Cancer Detection: A Study of 1,835 Paired Urine Samples with Clinical and Histological Correlation. *Cancer cytopathology.* 2013; 121(10):591-597.).

TABLE 2

Validation Results

| | Algorithm Negative | Algorithm Positive | |
|---|---|---|---|
| Pathology Negative | 621 | 76 | Specificity = 89.1% |
| Pathology Positive | 14 | 30 | Sensitivity = 68.2% |
| | NPV = 97.8% | PPV = 28.3% | Accuracy = 87.9% |

Example 2

Example 1 was repeated, using the same samples, with the Example 1 system further trained using available histological follow-up data. Additionally, a lower model decision point/threshold was applied for increased sensitivity.

Materials and Methods

Data Acquisition

All voided and instrumented urine specimens from both the lower and upper urinary tract included in this study were routinely prepared using ThinPrep technique. All cases were diagnosed using TPSRUC. Archival ThinPrep glass slides were scanned on an Aperio AT2 scanner (Leica) at 40× magnification with one Z-plane. The macro of each scanned image was checked to determine if the image quality was satisfactory. Whole slide images (WSI) were acquired using Aperio's standard JPEG compression. WSIs were de-identified and transferred to a Health Insurance Portability and Accountability Act (HIPAA)-compliant cloud environment for all computational development and validation procedures. For all cases the cytopathology diagnoses and available histological follow-up (up to one year following urine sample collection) were recorded. This study was approved by the institutional review board at the University of Pittsburgh.

Computational Analysis Pipeline

Figure 11:
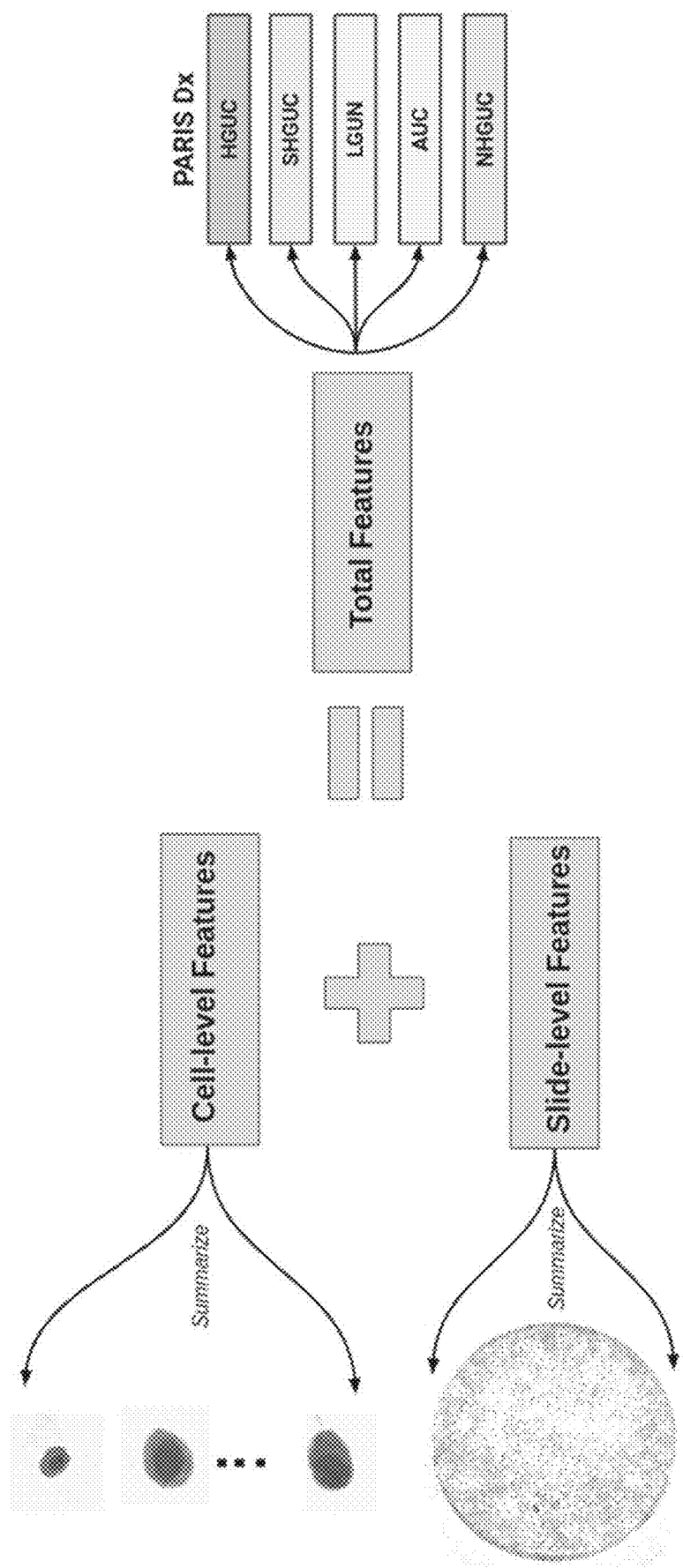
FIG. 11 is a schematic of a computational pipeline for WSI classification of urine cytology slides.

A computational pipeline with multiple tiers of models was developed for processing the WSI and predicting diagnosis (FIG. 11). QuPath[19] was used to perform cell detection, identifying all cells in a WSI. Centered cell images of size 150×150 pixels were extracted using the open source image processing software VIPS[20] and passed through a deep learning algorithm to detect urothelial cells. Images for all urothelial cells were then passed to six convolutional neural network (CNN) models trained to detect PARIS cytomorphological features (N/C ratio, hyperchromasia, chromatin coarseness, nuclear membrane irregularity) as well as models for cell degradation and overall malignancy. Potential cell clusters were separately identified using Density-Based Spatial Clustering of Applications with Noise (DBSCAN) and analyzed by a CNN model to detect true cell clusters. Cell feature and cell cluster scores were aggregated for the whole slide using histograms and summary statistics to generate a slide-level feature vector. A multi-class gradient boosting classifier was then trained on these summarized slide-level features to predict the cytology diagnosis. To improve performance with respect to histology diagnoses, an ensemble model was built to capture information from cytology as well as follow up histology diagnosis when available. Two gradient boosting classifiers were built for a) cases with just cytology diagnosis, and b) cases where the histology diagnosis was present. The output of both of these models, as well as the slide-level features, was then fed to a logistic regression model trained on the histology diagnoses through cross validation.

Cell Annotations

For urothelial cell detection, 8,037 cells were labeled as urothelial or non-urothelial (e.g. squamous, inflammatory cells) by three board-certified cytopathologists. Models based on the TPSRUC features were trained on 4,560 cell images each with 5 labels collected by one board-certified cytopathologist. Augmentation methods including rotation, hue, brightness, and sharpness were applied to cell images from both label sets. All annotations were collected using a web-based labeling tool.[21]

Algorithm Evaluation

For the purposes of evaluating binary performance metrics such as accuracy and sensitivity, we considered cytology diagnoses of Negative for High Grade Urothelial Carcinoma (NHGUC) and Atypical Urothelial Cells (AUC) as Negative, while Low Grade Urothelial Neoplasm (LGUN), Suspicious for High Grade Urothelial Carcinoma (SHGUC) and High Grade Urothelial Carcinoma (HGUC) were considered positive. Receiver operating curves were plotted by varying the positive class probability threshold, and the operating point was selected based on the optimal threshold on the validation set. The area under ROC (AUROC) confidence interval estimate was calculated using the DeLong method.[22]

Results

A total of 1,615 cases were used in the dataset to develop the algorithm and another 790 cases were subsequently employed for validation. Patient demographics and sample characteristics of the datasets utilized are summarized in Table 1. Cases with unsatisfactory image quality were excluded from the study (Table 2).

TABLE 1

Baseline characteristics of development and validation datasets

| Characteristics | Development Dataset (n = 1615) | Validation Dataset (n = 790) |
|---|---|---|
| Female, number (%) | 500 (31.0%) | 175 (22.1%) |
| Age, median years (standard deviation) | 72.7 (13.6) | 73.3 (10.2) |
| Negative for High Grade, number (%) | 848 (52.5%) | 599 (75.8%) |
| Atypical Urothelial Cells, number (%) | 229 (14.2%) | 141 (17.8%) |
| Suspicious for HGUC, number (%) | 243 (15.0%) | 30 (3.8%) |
| High Grade Urothelial Carcinoma, number (%) | 248 (15.4%) | 14 (1.8%) |
| Instrumented samples, number (%) | 263 (16.3%) | 40 (5.1%) |

HGUC = High Grade Urothelial Carcinoma

TABLE 2

Cases excluded from the study with insufficient scan quality

| Exclusion Reason | Development Dataset (n = 1615) | Validation Dataset (n = 790) |
|---|---|---|
| All case exclusions, number (%) | 179 (11.1%) | 48 (6.1%) |
| Virtually acellular sample, number (%) | 116 (7.2%) | 25 (3.2%) |
| Scan error, number (%) | 26 (1.6%) | 13 (1.6%) |
| Problematic image focus, number (%) | 37 (2.3%) | 10 (1.3%) |

The development dataset was enriched with positive examples of HGUC and LGUN. The training (development) dataset contained 1,436 cases that were of sufficient scan quality for analysis, of which 490 (30.3%) were diagnosed as SHGUC or HGUC. The separate test validation dataset was represented by approximately six months of routine, consecutive urine cytology cases signed out at an academic medical center with expertise in non-gynecologic cytopathology. In the validation set, 44 (5.6%) cases were diagnosed as SHGUC/HGUC.

Figure 12:
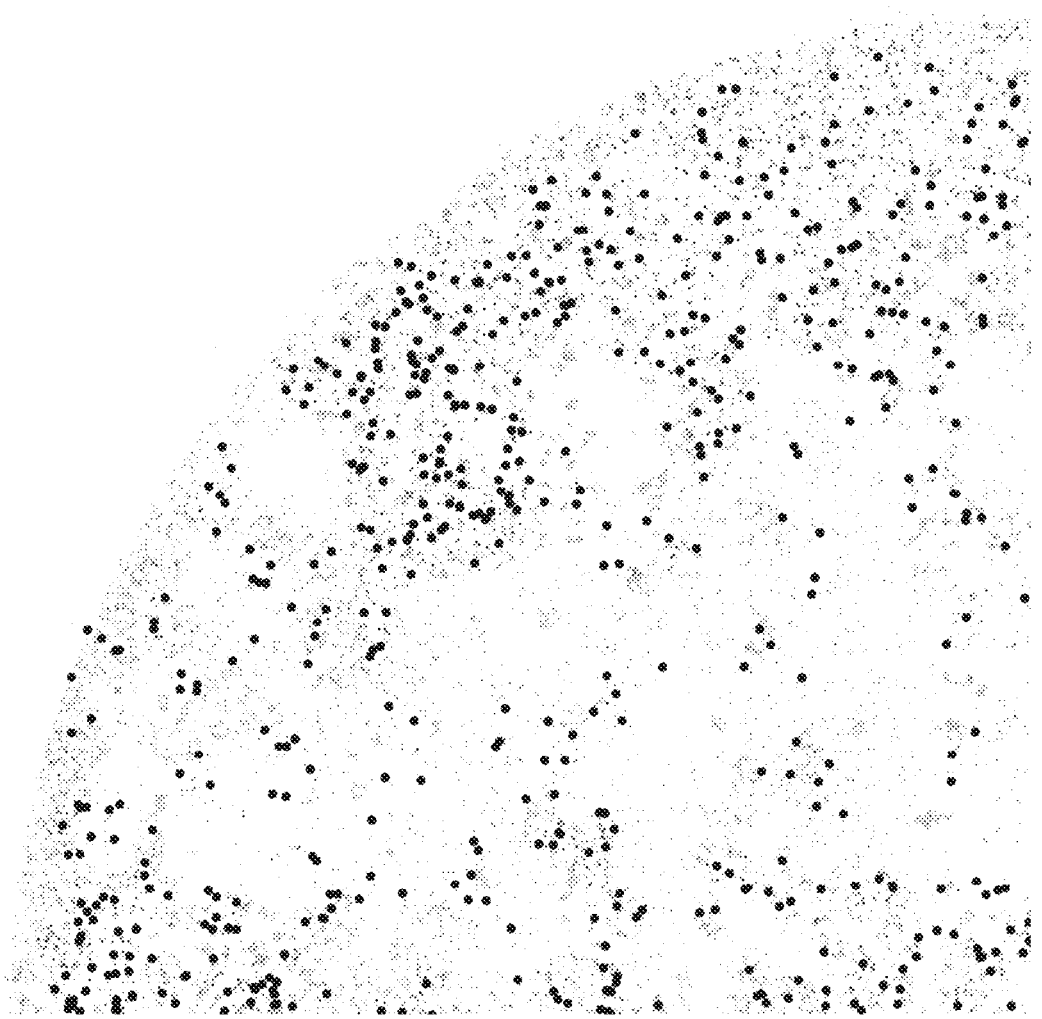
FIG. 12 is a visualization image of cells detected in a whole slide image. Only a quarter section view of a Thin-Prep cell spot is shown with all detected cells for a HGUC case. Suspected malignant urothelial cells are shown in red, normal urothelial cells in orange, and all other cells detected displayed in blue.
Figure 13:
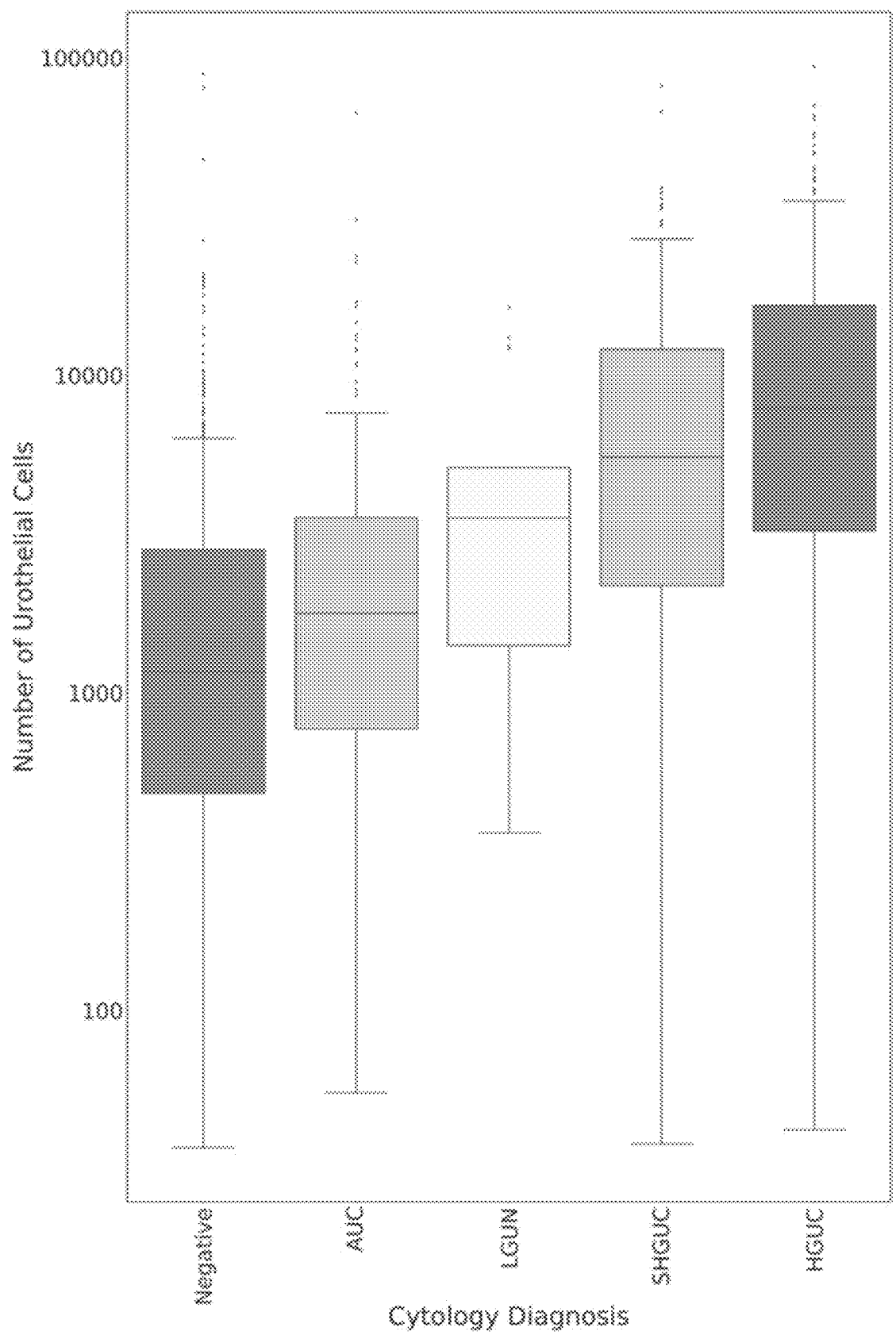
FIG. 13 is a graph of the number of urothelial cells detected per diagnosis (AUC=atypical urothelial cells, LGUN=low grade urothelial neoplasm, SHGUC=suspicious for high grade urothelial carcinoma, HGUC=high-grade urothelial carcinoma).
Figure 14A:
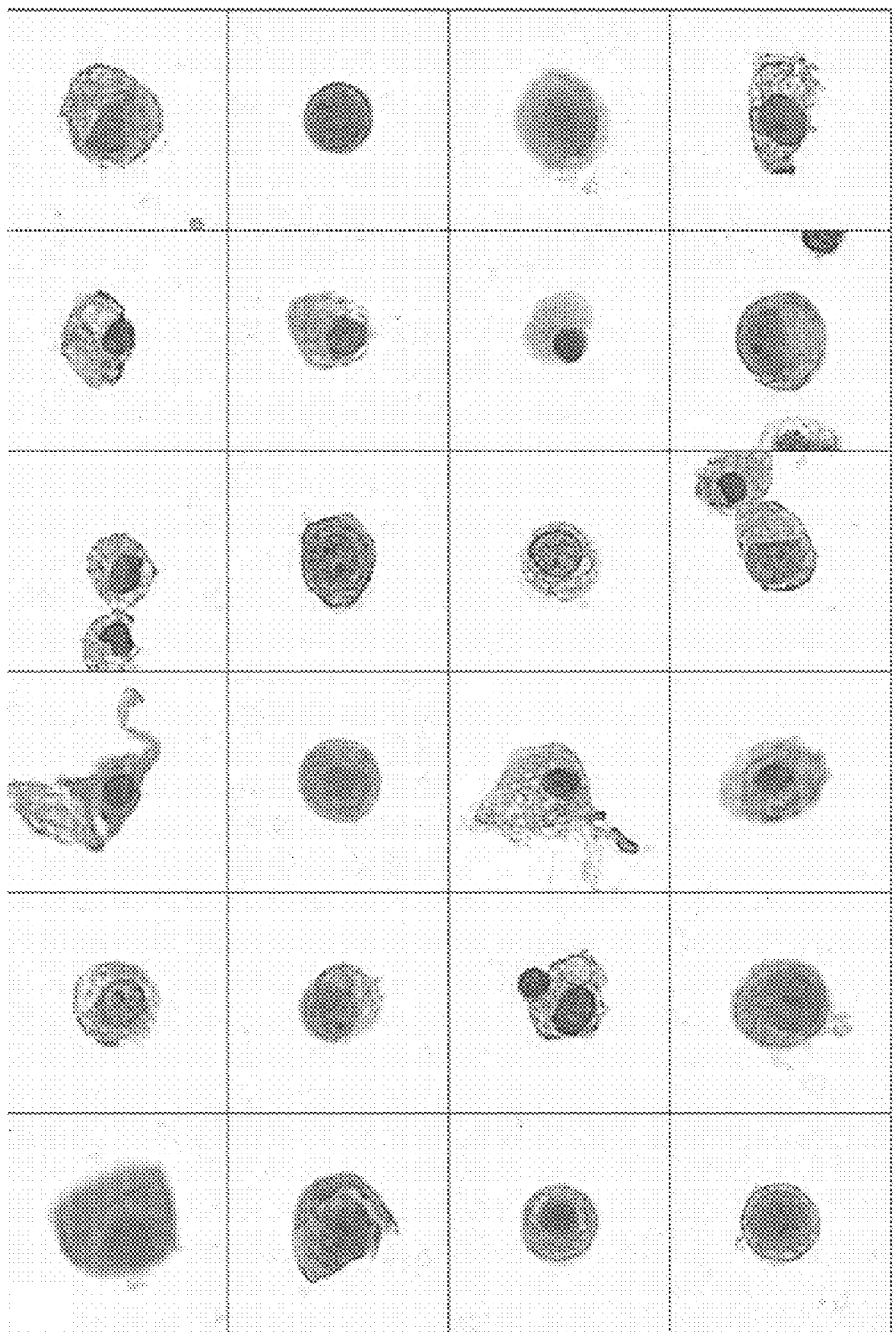
FIG. 14A is an exemplary urothelial cell gallery displaying algorithm results comprised of 24 cells with the "most atypical" PARIS features in a case that is negative for high grade urothelial carcinoma case.
Figure 14B:
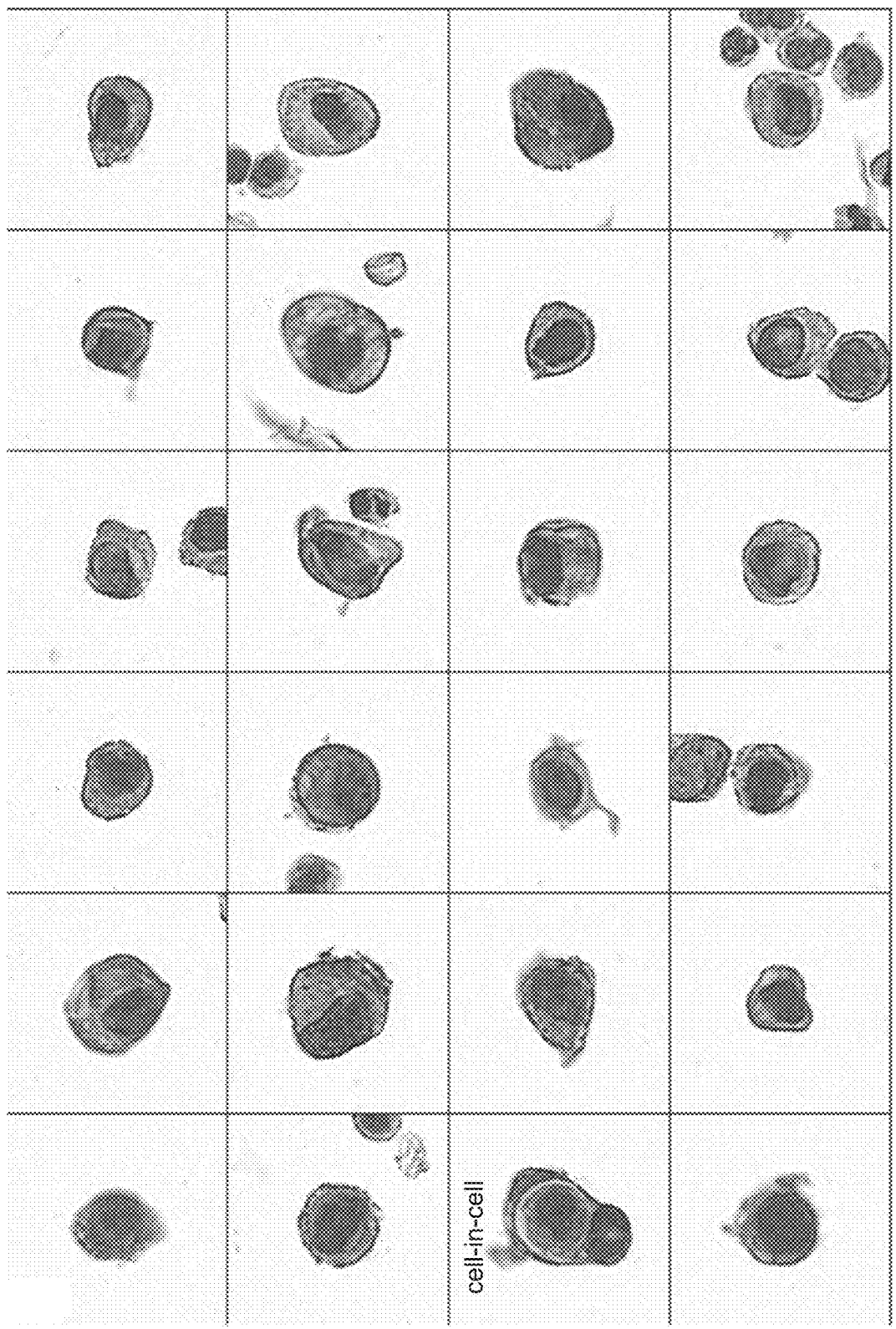
FIG. 14B is an exemplary urothelial cell gallery displaying algorithm results comprised of 24 cells with the "most atypical" PARIS features in a case that is high grade urothelial carcinoma case. Note that the urothelial cells in column 1 and row 3 demonstrate a cell-in-cell arrangement which is a typical finding in urothelial malignancy.

A total of 26 million individual potential cells were identified and analyzed, 1.9 million of which were detected by the algorithm as urothelial and the remainder were non-urothelial cells (e.g. squamous cells, inflammatory cells). An average of 36,000 cells were identified within each WSI. An example overlay image depicting all detected cells is shown in FIG. 12. Boxplots showing the number of urothelial cells detected per diagnostic category are shown in FIG. 13. High grade cases contained the most urothelial cells on average. Outliers were attributed to hypercellular cases and samples where the urine was instrumented, leading to a more populated sample. Example galleries composed of the 24 predicted most relevant cells for one negative case and one high grade case are presented in FIGS. 14A and 14B, respectively. In particular, FIG. 14B provides a gallery for a high-grade case exhibiting a cell-in-cell arrangement, as evidenced by the specimen shown in column 1 and row 3 in the figure.

Cell-in-cell arrangements can be beneficial in differentiating positive (HGUC or SHGUC) cases from negative or atypical cases. An iteration of a cell-in-cell classifier was analyzed and the number of identified cell-in-cell arrangements was summed for slides in the validation set (44 positive case and 698 negative cases/AUC). The identification of at least two CIC arrangements as the criteria for a positive case (and less than two for a negative case) resulted in the correct identification of 27 out of 44 positive cases and 600 out of 698 negative cases.

All digital slides in the validation set were processed by the algorithm with a median analysis time of 8 minutes per case.

The algorithm achieved an AUC of 0.88 (95% CI, 0.83-0.93). Using the optimal operating point, the algorithm's sensitivity was 79.5% (95% CI, 64.7-90.2) and specificity was 84.5% (95% CI, 81.6-87.1) for HGUC. While the algorithm incorrectly predicted only nine SHGUC/HGUC cases (9/742, 1.2%) as negative (Table 3), the overwhelming majority (8/9) of these particular cases were diagnosed as SHGUC rather than HGUC.

TABLE 3

Validation dataset performance of the algorithm at the optimal operating point

| | Algorithm Negative | Algorithm Positive | |
|---|---|---|---|
| Cytology Negative | 590 | 108 | Specificity = 84.5% |
| Cytology Positive | 9 | 35 | Sensitivity = 79.5% |
| | Negative Predictive Value = 98.5% | Positive Predictive Value = 24.5% | Accuracy = 84.2% |

In the subset of cases with available histological follow-up (148/742, 19.9%), the accuracy of the algorithm (86/148, 58.1%) exceeded that of the cytology diagnosis alone (68/148, 45.9%) in predicting low- or high-grade urothelial carcinoma. The algorithm's performance for each sample collection type is shown in Table 4. The algorithm shows an AUC of 0.96 and 0.91 for instrumented and voided samples, respectively, and is much more sensitive overall when the urine sample collection type is known.

TABLE 4

Validation dataset performance by sample collection type

| Sample Collection Type | Sensitivity (%) | Specificity (%) | AUC |
|---|---|---|---|
| Instrumented (n = 35) | 100 | 70.5 | 0.97 |
| Voided (n = 557) | 80.6 | 87.3 | 0.91 |
| Not Otherwise Specified (n = 150) | 71.4 | 77.6 | 0.72 |

DISCUSSION

Urine samples are one of the most common non-gynecological specimens typically seen by cytology laboratories. The success in developing a computational algorithm to analyze urine cytology cases as described herein can improve pathologist productivity by improving the time taken to screen WSIs, akin to what is currently used for Pap test screening. It may also improve diagnostic accuracy as visual quantification of criteria such as N/C ratio are challenging for humans to accurately reproduce.[10, 11] Several early investigators have already demonstrated that image analysis of urine cytology was superior to human review.[23-26] However, Gelwan et al reported greater inter-observer variability than routine manual review when urinary cytology specimens were evaluated using the Cell Solutions BestCyte Cell Sorter imaging system.[27] This may be attributed to the fact that the image algorithm utilized was designed specifically for analyzing cervical cytology cases, whereas the systems and methods described herein are designed specifically for urine cytology cases.

Better image analysis results have been demonstrated when applying neural network models, specifically developed to analyze urothelial cells.[18,24,28] Indeed, Pantazopoulos et al reported a sensitivity of 94.5% and specificity of 100% for detecting urothelial carcinoma in urine cytology specimens.[28] Vaickus et al are commended for developing an equivalent hybrid deep learning and morphometric algorithm to analyze urine cytology specimens.[18] However, Vaickus et al used a much smaller sample size (n=217) of carefully selected cases, compared to the 2,405 cases that used in the example study described herein. The validation performance described herein was on consecutive urine cytology cases, as the cases came in for interpretation during a time period. For example, there was no enrichment of certain classes (high grade, etc) that are of normally low prevalence, thus providing a better simulation of clinical practice. This enables additional confidence about the performance and generalizability of the model described herein through the introduction of extra variation. The dataset described herein additionally included both LGUN and HGUC cases to represent the entire spectrum of urothelial neoplasms. Moreover, whereas Vaickus et al generated predictions predominantly on cells at the sub-image level, the systems and methods described herein employed a combination of both cell-level and whole slide-level features. The model described herein does not perform subsampling; rather, it leverages all available information from the slide, so that there is confidence that rare or obscured malignant cells are not missed.

Limitations of the study described herein include that the cases utilized were obtained from a tertiary academic medical center that receives a disproportionate number of uncommon (e.g. neobladder, upper urinary tract) and difficult (e.g. polyoma virus infected transplant patients, non-urothelial malignancy) cases. Also, the WSIs were acquired using only one Z-plane. Unlike two dimensional (2D) histopathology sections, cytology cases such as urine specimens are typically composed of both single cells and three dimensional (3D) cell clusters which are harder to focus on in only one depth of field. In addition, obscuring material (e.g. blood) and overlapping inflammatory cells may further negatively impact focus. This problem can be addressed by Z-stacking[29,30], which may be addressed in future digital cytology whole slide scanners.

The use of digital image algorithms in pathology enables not only automation and computer-assisted diagnosis, but also offers the potential to standardize diagnoses, improve accuracy and better explore pathologic diseases.[1,31] In under eight minutes the system and method described herein was able to detect, classify and analyze on average 36,000 cells per case. When doing so, it is unclear exactly why the HGUC cases contained the most urothelial cells. Perhaps this can be explained by increased shedding of malignant urothelial cells in urine samples. TPSRUC incorporates relatively few major and minor criteria to assist in the interpretation of cases. Moreover, recent research indicates that some of the quantitative criteria used in TPSRUC such as N/C ratio for the SHGUC and HGUC categories may be inaccurate.[32] By comparison, the computational analysis pipeline developed and described herein not only incorporates features from The Paris System, but includes additional cell-level features (e.g. degradation, malignancy, focal score) and whole slide-level features (e.g. cluster counts, cell types, cell-in-cell arrangement count, overall malignant cell counts). Given that the morphology of individually shed urothelial cells is often not well preserved in urine, it was postulated that it was particularly important to train the algorithm of the systems and methods described herein to identify degraded cells.

The use of a digital gallery to review analyzed cases offers a novel approach to cytology cases. Such galleries for the Pap test have been shown to improve the digital cytology review experience for cytotechnologists and increase efficiency.[33] It is easy to see why the systems and methods described herein can help augment the analysis of urine cytology cases.

REFERENCES

1. Khalbuss W E, Monaco S E, Pantanowitz L. Quick compendium of cytopathology. ASCP Press, Chicago. 2013. Pages 183-210.
2. McIntire P J, Khan R, Hussain H, Pambuccian S E, Wojcik E M, Barkan G A. Negative predictive value and sensitivity of urine cytology prior to implementation of The Paris System for Reporting Urinary Cytology. Cancer Cytopathol 2019; 127(2):125-31.
3. McCroskey Z, Pambuccian S E, Kleitherms S, et al. Accuracy and interobserver variability of the cytologic diagnosis of low-grade urothelial carcinoma in instrumented urinary tract cytology specimens. Am J Clin Pathol 2015; 144(6):902-8.
4. Lee P J, Owens C L, Lithgow M Y, Jiang Z, Fischer A H. Causes of false-negative for high-grade urothelial carcinoma in urine cytology. Diagn Cytopathol 2016; 44(12): 994-9.
5. Reid M D, Osunkoya A O, Siddiqui M T, Looney S W. Accuracy of grading of urothelial carcinoma on urine cytology: an analysis of interobserver and intraobserver agreement. Int J Clin Exp Pathol 2012; 5(9):882-91.
6. Barkan G A, Wojcik E M, Nayar R, et al. The paris system for reporting urinary cytology: the quest to develop a standardized terminology. Acta Cytol 2016; 60(3):185-97.
7. Brimo F, Auger M, Elsheikh T M, et al. Suspicious for High-Grade Urothelial Carcinoma (Suspicious). In: Rosenthal D L, Wojcik E M, Kurtycz D F I, editors. The paris system for reporting urinary cytology. Cham: Springer International Publishing; 2016. p. 49-60.
8. VandenBussche C J. A review of the Paris system for reporting urinary cytology. Cytopathology 2016; 27(3): 153-6.
9. Northrup V, Acar B C, Hossain M, Acker M R, Manuel E, Rahmeh T. Clinical follow up and the impact of the Paris system in the assessment of patients with atypical urine cytology. Diagn Cytopathol 2018; 46(12):1022-30.
10. Long T, Layfield L J, Esebua M, Frazier S R, Giorgadze D T, Schmidt R L. Interobserver reproducibility of The Paris System for Reporting Urinary Cytology. Cytojournal 2017; 14:17.
11. Layfield L J, Esebua M, Frazier S R, et al. Accuracy and reproducibility of nuclear/cytoplasmic ratio assessments in urinary cytology specimens. Diagn Cytopathol 2017; 45(2):107-12.
12. Pantanowitz L. Automated pap tests. In: Practical informatics for cytopathology. Pantanowitz L, Parwani A V (editors). Springer, New York. 2014; 1:147-155.
13. William W, Ware A, Basaza-Ejiri A H, Obungoloch J. A review of image analysis and machine learning techniques for automated cervical cancer screening from pap-smear images. Comput Methods Programs Biomed 2018; 164: 15-22.
14. Janowczyk A, Madabhushi A. Deep learning for digital pathology image analysis: A comprehensive tutorial with selected use cases. J Pathol Inform 2016; 7:29.
15. Song Y, Zhang L, Chen S, Ni D, Lei B, Wang T. Accurate segmentation of cervical cytoplasm and nuclei based on multiscale convolutional network and graph partitioning. IEEE Trans Biomed Eng 2015; 62(10):2421-33.
16. Dey P, Logasundaram R, Joshi K. Artificial neural network in diagnosis of lobular carcinoma of breast in fine-needle aspiration cytology. Diagn Cytopathol 2013; 41(2):102-6.
17. Momeni-Boroujeni A, Yousefi E, Somma J. Computer-assisted cytologic diagnosis in pancreatic FNA: An application of neural networks to image analysis. Cancer Cytopathol 2017; 125(12):926-33.
18. Vaickus L J, Suriawinata A A, Wei J W, Liu X. Automating the Paris System for urine cytopathology-A hybrid deep-learning and morphometric approach. Cancer Cytopathol 2019; 127(2):98-115.
19. Bankhead P, Loughrey M B, Fernandez J A, et al. QuPath: Open source software for digital pathology image analysis. Sci Rep 2017; 7(1):16878.
20. Martinez K, Cupitt J. VIPS—a highly tuned image processing software architecture. In: IEEE International Conference on Image Processing 2005. IEEE; 2005. p. 11-574.
21. Pantanowitz L, Allen E, Callenberg K, et al. Community crowdsourcing tool to expedite annotations for deep learning in pathology. J Pathol Inform 2018; 9(50):S14.
22. DeLong E R, DeLong D M, Clarke-Pearson D L. Comparing the areas under two or more correlated receiver operating characteristic curves: a nonparametric approach. Biometrics 1988; 44(3):837-45.
23. Melder K K, Koss L G. Automated image analysis in the diagnosis of bladder cancer. Appl Opt 1987; 26(16):3367-72.
24. van der Poel H G, Boon M E, van Stratum P, et al. Conventional bladder wash cytology performed by four experts versus quantitative image analysis. Mod Pathol 1997; 10(10):976-82.
25. Vriesema J L J, van der Poel H G, Debruyne F M J, Schalken J A, Kok L P, Boon M E. Neural network-based digitized cell image diagnosis of bladder wash cytology. Diagn Cytopathol 2000; 23(3):171-9.
26. Wied G L, Dytch H, Bibbo M, Bartels P H, Thompson D. Artificial intelligence-guided analysis of cytologic data. Anal Quant Cytol Histol 1990; 12(6):417-28.
27. Gelwan E, Zhang M L, Allison D B, et al. Variability among observers utilizing the CellSolutions BestCyte Cell Sorter imaging system for the assessment of urinary tract cytology specimens. J Am Soc Cytopathol 2019; 8(1):18-26.
28. Pantazopoulos D, Karakitsos P, Iokim-Liossi A, Pouliakis A, Botsoli-Stergiou E, Dimopoulos C. Back propagation neural network in the discrimination of benign from malignant lower urinary tract lesions. J Urol 1998; 159 (5):1619-23.
29. Mukherjee M, Radio S, Wedel W, et al. Investigation of scanning parameters for thyroid fine needle aspiration cytology specimens: A pilot study. J Pathol Inform 2015; 6(1):43.
30. Donnelly A, Mukherjee M, Lyden E, et al. Optimal z-axis scanning parameters for gynecologic cytology specimens. J Pathol Inform 2013; 4(1):38.
31. Hang J-F, Charu V, Zhang M L, VandenBussche C J. Digital image analysis supports a nuclear-to-cytoplasmic ratio cutoff value of 0.5 for atypical urothelial cells. Cancer Cytopathol 2017; 125(9):710-6.
32. McIntire P J, Snow J T, Elsoukkary S S, et al. Digital image analysis supports a nuclear-to-cytoplasmic ratio cutoff value below 0.7 for positive for high-grade urothelial carcinoma and suspicious for high-grade urothelial carcinoma in urine cytology specimens. Cancer Cytopathol 2019; 127(2):120-4.
33. Mitchell C, Callahan S, Tata L, Harrington S, Ludlow E. Improving the digital cytology review experience may lead to increased efficiency. J Am Soc Cytopathol 2018; 7(5):565.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A method, comprising:
identifying, by a system of one or more computers, a first feature vector that represents cytomorphologic criteria for each of one or more individual cells within a plurality of cells in at least a portion of a whole specimen slide image, wherein the first feature vector includes a plurality of cell-level features;
identifying, by the system, a second feature vector indicative of slide-level features, wherein identifying the second feature vector comprises:
aggregating the plurality of cell-level features; and based on the aggregation, determining a set of metrics representing the whole specimen slide image; and
providing, by the system, the first and the second feature vectors to a machine learning model configured to generate a plurality of feature scores, each feature score corresponding to each feature in the first and the second feature vectors, wherein the feature score is predictive of a presence or absence of a disease or disease type identified in the whole specimen slide image; and
determining, by the system and based on the plurality of feature scores, the presence or absence of a disease or disease type.

2. The method of claim 1, further comprising, prior to identifying the first feature vector:
receiving, by the system, an image of a whole specimen slide comprising a plurality of biological cells;
detecting, by the system, at least a portion of each of one or more individual cells within the plurality of cells; and
determining, by the system, spatial coordinates for each of the one or more individual cells.

3. The method of claim 2, further comprising extracting, by the system, for each of the one or more individual cells, an extracted image of the individual cell, wherein the cell is centered on the extracted image, each extracted image representing an independent individual cell.

4. The method of claim 3, further comprising:
processing, by the system, the one or more extracted images to generate a cell type score for each extracted image; and
extracting, by the system, a set of one or more of the extracted images having a cell type score within a predetermined range, wherein the cell type score a likelihood that the cell is a target cell type.

5. The method of claim 1, further comprising ranking, by the system, the individual cells based on the plurality of feature scores.

6. The method of claim 1, further comprising classifying, by the system and using a Gaussian mixture model, each of the individual cells into one of a plurality of predetermined cell-type clusters based on the plurality of feature scores.

7. The method of claim 1, wherein the machine learning model is a convolutional neural network model.

8. The method of claim 1, wherein the plurality of cell-level features is selected from the group consisting of a nuclear-to-cytoplasmic ratio, nuclear hyperchromasia, chromatin coarseness, nuclear membrane irregularity, cellular degradation, malignancy classifier, malignancy value, focal score, nuclear-to-cytoplasmic pixel ratio, cell-in-cell arrangements, and combinations thereof.

9. The method of claim 1, further comprises generating summary statistics based on the first feature vector.

10. The method of claim 9, wherein the summary statistics are selected from the group consisting of mean, median, standard deviation, variance, kurtosis, or skew, histograms, principal components analysis, and combinations thereof.

11. The method of claim 1, further comprising:
providing, by the system, one or more outputs indicative of the presence or absence of a disease or disease type identified in the whole specimen slide, wherein the one or more outputs are selected from the group consisting of summary statistics, a cell type cluster score, one or more feature scores, an image of one or more cells, a composite image having a plurality of images of multiple cells, and combinations thereof.

12. The method of claim 4, further comprising, prior to processing the one or more extracted images, removing, by the system, background noise in each of the extracted images.

13. The method of claim 1, wherein determining the presence or absence of a disease or disease type comprises:
obtaining the plurality of feature scores from the machine learning model trained on at least one of a group comprising cytomorphologic criteria and histologic criteria.

14. The method of claim 1, wherein the machine learning model is trained using both cytomorphologic criteria and histologic criteria.

15. The method of claim 1, wherein the machine learning model is trained using histological criteria when available and cytomorphologic criteria when the histological criteria is not available.

16. The method of claim 1, wherein the machine learning model is trained by combining a histological test with a cytomorphologic test.

17. The method of claim 16, wherein the combining of the histological test with the cytomorphologic tests comprises a comparison of a histological confidence value generated by the histologic test with a cytomorphologic confidence value generated by the cytomorphologic test.

18. The method of claim 1, wherein the disease or disease type comprises high grade urothelial carcinoma, suspicious for high grade urothelial carcinoma, low grade urothelial neoplasia, atypical urothelial cells, and negative for high grade urothelial carcinoma.

19. The method of claim 1, further comprises evaluating effectiveness of a cancer intervention measure in a subject having or at risk for developing a cancer, wherein the whole specimen slide image is derived from the subject
applying at least one intervention measure that is commensurate with treating or preventing the cancer; and
determining the effectiveness of the intervention measure.

20. The method of claim 1, further comprising:
displaying an image of a whole specimen slide including biological cells, the image overlaid with a visual representation of a prediction score for each of the one or more individual cells identified in the slide.

21. The method of claim 20, wherein the prediction score provides a visual indication of an importance score for at least some of the cells based on the respective cell's importance in determining the presence or absence of a disease or disease type.

22. The method of claim 20, wherein the prediction score provides a visual indication of a point on a severity scale indicative of a severity of the disease or disease type.

23. The method of claim 1, further comprising:
displaying a single composite displayed image comprising a plurality of selected individual cell images extracted from at least the portion of the whole specimen slide image.

* * * * *

UNITED STATES PATENT AND TRADEMARK OFFICE
CERTIFICATE OF CORRECTION

PATENT NO. : 11,508,168 B2  
APPLICATION NO. : 16/653571  
DATED : November 22, 2022  
INVENTOR(S) : Allen et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 318 days.

Signed and Sealed this  
Sixth Day of February, 2024

Katherine Kelly Vidal  
*Director of the United States Patent and Trademark Office*